(12) United States Patent
Nitta et al.

(10) Patent No.: US 8,500,640 B2
(45) Date of Patent: Aug. 6, 2013

(54) BLOOD VESSEL FUNCTION INSPECTING APPARATUS

(75) Inventors: Naotaka Nitta, Tsukuba (JP); Hiroshi Masuda, Nagoya (JP)

(73) Assignees: National Institute of Advanced Industrial Science and Technology, Tokyo (JP); Unex Corporation, Nagoya-Shi (JP)

( * ) Notice: Subject to any disclaimer, the term of this patent is extended or adjusted under 35 U.S.C. 154(b) by 46 days.

(21) Appl. No.: 13/377,357

(22) PCT Filed: Jun. 9, 2009

(86) PCT No.: PCT/JP2009/060562
§ 371 (c)(1),
(2), (4) Date: Dec. 16, 2011

(87) PCT Pub. No.: WO2010/143271
PCT Pub. Date: Dec. 16, 2010

(65) Prior Publication Data
US 2012/0095332 A1 Apr. 19, 2012

(51) Int. Cl.
*A61B 8/00* (2006.01)
*A61B 5/02* (2006.01)
(52) U.S. Cl.
USPC ............................ 600/438; 600/437; 600/481
(58) Field of Classification Search
USPC .. 600/437, 438, 481, 485, 504, 508; 382/128; 73/53.04
See application file for complete search history.

(56) References Cited

FOREIGN PATENT DOCUMENTS

| JP | A-2003-144395 | 5/2003 |
|----|---------------|--------|
| JP | A-2006-166974 | 6/2006 |
| JP | B2-3785084    | 6/2006 |
| JP | A-2007-175127 | 7/2007 |

OTHER PUBLICATIONS

Nitta, N. et al., "Hemodynamic Force Imaging Based on Ultrasonic Blood Flow Measurement," *Papers of Technical Meeting On Medical and Biological Engineering*, Dec. 16, 2006, pp. 13-19 (with Abstract).
International Search Report issued in International Application No. PCT/JP2009/060562 on Aug. 4, 2009 (with translation).

*Primary Examiner* — Michael Rozanski
(74) *Attorney, Agent, or Firm* — Oliff & Berridge, PLC

(57) ABSTRACT

A blood vessel function inspecting apparatus including blood flow velocity distribution measuring portion for measuring a blood flow velocity distribution within a blood vessel in a non-invasion manner with ultrasonic waves before releasing of the blood vessel from a blood flow obstruction or after a blood vessel diameter measuring time period; viscosity-shear rate relationship calculating portion; and blood shear stress calculating portion for measuring a blood flow velocity within the blood vessel, concurrently with the measurement of a change ratio of the diameter of the blood vessel within the predetermined blood vessel diameter measuring time period after releasing of the blood vessel from the blood flow obstruction, and calculating a blood shear stress on the basis of a measured blood flow velocity, and according to a viscosity-shear rate relationship.

12 Claims, 14 Drawing Sheets

BLOOD VESSEL FUNCTION INSPECTING APPARATUS

TECHNICAL FIELD

The present invention relates to techniques for non-invasion evaluation of a dilatation function of a blood vessel of a live body.

BACKGROUND ART

There is know a blood vessel function inspecting apparatus for measuring a blood flow velocity distribution within a blood vessel, by ultrasonic Doppler effect measurement. Patent Document 1 discloses an example of such a blood vessel function inspecting apparatus. The blood vessel function inspecting apparatus disclosed in this Patent Document 1 is configured to calculate a blood viscosity distribution and a blood shear rate distribution within the blood vessel, on the basis of the blood flow velocity distribution measured as described above. The blood vessel function inspecting apparatus is further configured to calculate a blood shear stress distribution on the basis of the calculated blood viscosity distribution and blood shear rate distribution. The calculation of the above-described blood viscosity distribution by the blood vessel function inspecting apparatus on the basis of the above-described blood flow velocity distribution is implemented by calculation according to the well known Navier-Stokes equations.

In the well known FMD inspection, a change ratio of the diameter of the blood vessel after releasing of the blood vessel from blood flow obstruction is measured. It is know that a change (an increase) of the diameter of the blood vessel is caused by a stimulus in the form of a shear stress. In this respect, the detection of the above-described shear stress is effective to implement the FMD inspection. Patent Document 2 discloses a blood vessel function inspecting apparatus configured to calculate the above-described shear stress for the FMD inspection.

PRIOR ART DOCUMENTS

Patent Documents
  Patent Document 1: JP-2006-166974A
  Patent Document 2: JP-3785084 B2

SUMMARY OF THE INVENTION

Object Achieved by the Invention

The blood vessel function inspecting apparatus disclosed in the above-identified Patent Document 2 calculates the above-described shear stress on the basis of the blood viscosity, so that this blood viscosity is required to be obtained before calculation of the shear stress. This blood viscosity is usually measured with a measuring instrument, with respect to a blood drawn from a subject person. However, the blood viscosity varies after drawing of the blood, and also changes with a change of the blood flow velocity (more precisely, with a change of the shear rate). For these reasons, there is an unknown problem that the calculation of the blood shear stress on the basis of the viscosity of the drawn blood is not sufficiently accurate.

It is not known but is considered possible that the blood flow velocity distribution which varies with time is measured successively for the FMD inspection during a time period of measurement of the diameter change ratio of the blood vessel after releasing of the blood vessel from the blood flow obstruction, so that the blood viscosity distribution is calculated on the basis of all values of the blood flow velocity distribution measured during the time period of measurement. However, the calculation of the blood viscosity distribution requires calculation according to the Navier-Stokes equations, for all values of the blood flow velocity distribution obtained during the time period of measurement, giving rise to a problem of an increase of a load of arithmetic operation for the calculation.

The present invention was made in view of the background art described above. It is accordingly an object of this invention to provide a blood vessel function inspecting apparatus which permits accurate calculation of a blood shear stress for measurement of a change ratio of a diameter of a blood vessel after releasing of the blood vessel from blood flow obstruction, with a reduced load of arithmetic operation for the calculation.

Means for Achieving the Object

The object indicated above is achieved according to the invention, which provides a blood vessel inspecting apparatus provided with (a) blood vessel diameter measuring means for measuring a change ratio of a diameter of a blood vessel within a live body in a non-invasion manner with ultrasonic waves irradiated toward the blood vessel during a predetermined blood vessel diameter measuring time period after releasing of the blood vessel from blood flow obstruction, the blood vessel function inspecting apparatus being characterized by comprising (b) blood flow velocity distribution measuring means for measuring a blood flow velocity distribution within the above-described blood vessel in a non-invasion manner with the above-described ultrasonic waves before the above-described releasing of the blood vessel from the blood flow obstruction or after the above-described blood vessel diameter measuring time period, (c) viscosity-shear rate relationship calculating means for calculating a viscosity-shear rate relationship between a blood viscosity and a blood shear rate, on the basis of the above-described blood flow velocity distribution measured by the above-described blood flow velocity distribution measuring means, and (d) blood shear stress calculating means for calculating a blood flow velocity within the above-described blood vessel, concurrently with the measurement of the above-described change ratio of the diameter of the blood vessel within the above-described predetermined blood vessel diameter measuring time period after the above-described releasing of the blood vessel from the blood flow obstruction, and calculating a blood shear stress on the basis of the above-described measured blood flow velocity, and according to the above-described viscosity-shear rate relationship.

Advantages of the Invention

According to the present invention described above, accordingly, it is possible to calculate the above-described viscosity-shear rate relationship specific to the blood vessel and the blood, on the basis of the state of flow of the blood through the blood vessel under inspection. Therefore, it is possible to accurately calculate the blood shear stress according to this viscosity-shear rate relationship. In addition, once the above-described viscosity-shear rate relationship is calculated, the blood shear stress can be subsequently calculated with a low load of arithmetic operation. Furthermore, it is possible to compare and evaluate a plurality of results of the FMD inspection by reference to the blood shear stress, for example, which represents an amount of stimulus that causes dilatation of the blood vessel diameter after the blood vessel releasing from the blood flow obstruction.

Preferably, (a) the above-described blood flow velocity distribution measuring means measures the above-described blood flow velocity distribution before the above-described releasing of the blood vessel from the blood flow obstruction, and (b) the above-described viscosity-shear rate relationship calculating means calculates the viscosity-shear rate relation before the above-described releasing of the blood vessel from the blood flow obstruction. In this case, the blood shear stress can be calculated in the real-time processing fashion for the FMD evaluation, with a low load of arithmetic operation, concurrently with the measurement of the change ratio of the diameter of the blood vessel after the blood vessel releasing, without requiring calculations after the blood vessel releasing during a time period from the measurement of the blood flow velocity to the calculation of the blood viscosity, which measurements would cause a high load of arithmetic operation, such as a calculation according to the Navier-Stokes equations. Further, this manner of calculation of the blood shear stress in the real-time processing fashion makes it possible to quickly obtain the index value for the FMD inspection.

Also preferably, the blood shear stress calculating means is provided with (a) first blood flow velocity measuring means for measuring an average blood flow velocity within the above-described blood vessel during the above-described predetermined blood vessel diameter measuring time period after the above-described releasing of the blood vessel from the blood flow obstruction, concurrently with the measurement of the change ratio of the diameter of the above-described blood vessel, (b) first blood shear rate calculating means for calculating the blood shear rate on the basis of the above-described average blood flow velocity measured by the above-described first blood flow velocity measuring means, (c) first blood viscosity calculating means for calculating the blood viscosity on the basis of the above-described blood shear rate calculated by the above-described first blood shear rate calculating means, and according to the above-described viscosity-shear rate relationship calculated by the above-described viscosity-shear rate relationship calculating means, and (d) first blood shear stress calculating means for calculating the blood shear stress on the basis of the above-described blood shear rate calculated by the above-described first blood shear rate calculating means and the above-described blood viscosity calculated by the above-described first blood viscosity calculating means. Accordingly, the measurement of the above-described average blood flow velocity makes it possible to reduce the load of arithmetic operation during a time period from the measurement of the average blood flow velocity to the calculation of the blood viscosity, so that the blood shear stress can be calculated in the real-time processing fashion, concurrently with the measurement of the average blood flow velocity, without requiring the apparatus to have a high capacity of arithmetic operation.

Also preferably, the above-described first blood shear rate calculating means calculates the above-described blood shear rate by dividing the above-described average blood flow velocity by the above-described diameter of the blood vessel. In this case, the blood shear rate can be efficiently calculated from the average blood flow velocity, making it possible to reduce a load of arithmetic operation of the first blood shear rate calculating means. As a result, the blood shear stress can be calculated in the real-time processing fashion, concurrently with the measurement of the average blood flow velocity, with a reduced load of arithmetic operation. In this connection, it is noted that since the above-described average blood flow velocity and diameter of the blood vessel change with the time, the average blood flow velocity and the diameter of the blood vessel used to calculate the above-described blood shear rate are measured concurrently in synchronization with each other.

Also preferably, the above-described average blood flow velocity is an average of values of the blood flow velocity within the above-described blood vessel for each heart beat. In this case, the above-described first blood shear stress calculating means calculates the blood shear stress for each heart beat, so that the load of arithmetic operation can be made lower than in the case wherein a plurality of values of the blood shear stress are calculated during the time period of one heart beat.

Also preferably, the above-described first blood shear stress calculating means calculates the above-described blood shear stress for each heart beat within the above-described predetermined blood vessel diameter measuring time period. In this case, the blood shear stress can be calculated in a real-time processing fashion, so that the index value for the FMD inspection can be quickly obtained.

Also preferably, the above-described viscosity-shear rate relationship calculating means calculates a distribution of the blood viscosity and a distribution of the blood shear rate on the basis of the above-described blood flow velocity distribution measured by the above-described blood flow velocity distribution measuring means, and calculates the above-described viscosity-shear rate relationship on the basis of values of the blood viscosity and values of the blood shear rate, which are extracted from the distribution of the blood viscosity and the distribution of the blood shear rate, respectively, and which respectively correspond to a plurality of predetermined points within the above-described blood vessel. In this case, it is possible to more accurately calculate the above-described viscosity-shear rate relationship specific to the blood vessel and blood under inspection.

Also preferably, the above-described viscosity-shear rate relationship calculating means calculates the above-described blood viscosity distribution on the basis of the above-described blood flow velocity distribution measured by the above-described blood flow velocity distribution measuring means, and according to Navier-Stokes equations stored in a memory. In this case, the blood vessel function inspecting apparatus is practically operable to calculate the blood viscosity distribution on the basis of the blood flow velocity distribution.

Also preferably, (a) the above-described blood shear stress calculating means is provided with: second blood flow velocity measuring means for measuring the blood flow velocity distribution within the above-described blood vessel during the above-described predetermined blood vessel diameter measuring time period after the above-described releasing of the blood vessel from the blood flow obstruction, concurrently with the measurement of the above-described diameter of the blood vessel; second blood shear rate calculating means for calculating a maximum value of the blood shear rate on the basis of the above-described blood flow velocity distribution measured by the above-described second blood flow velocity measuring means; second blood viscosity calculating means for calculating the blood viscosity on the basis of the above-described maximum value of the blood shear rate calculated by the above-described second blood shear rate calculating means, and according to the above-described viscosity-shear rate relationship calculated by the above-described viscosity-shear rate relationship calculating means; and second blood shear stress calculating means for calculating the blood shear stress on the basis of the above-described maximum value of the blood shear rate calculated by the above-described second blood shear rate calculating means and the above-described blood viscosity calculated by the above-described second blood viscosity calculating means, during the above-described predetermined blood vessel diameter measuring time period, and (b) wherein the above-described first blood flow velocity measuring means measures the above-described average blood flow velocity if a predetermined condition for changing a method of arithmetic operation is satisfied, and the above-described second blood flow velocity measuring means measures the above-described blood flow velocity distribution if the above-described predetermined condition for changing the method of arithmetic operation is not satisfied. In this case, the manner of calculating the blood shear stress can be changed according to the estimated load of arithmetic operation after the blood vessel releasing from the blood flow obstruction, for example, depending upon whether the predetermined condition for changing the method of arithmetic operation is satisfied or not, in view of a considered tendency that the load of arithmetic operation of the above-described second blood shear stress calculating means to calculate the blood shear stress is higher than that of the above-described first blood shear stress calculating means, although the accuracy of calculation of the blood shear stress by the second blood shear stress calculating means is higher than that by the first blood shear stress calculating means.

Also preferably, the blood vessel function inspecting apparatus further comprises index value calculating means for calculating a ratio between a value relating to the above-described blood shear stress calculated by the above-described first blood shear stress calculating means or the above-described second blood shear stress calculating means, and a maximum value of the change ratio of the diameter of the above-described blood vessel after the blood vessel releasing measured by the above-described blood vessel diameter measuring means. In this case, a result of measurement of the change ratio of the diameter of the above-described blood vessel can be evaluated by reference to the blood shear stress. For instance, a plurality of results of the FMD inspection can be compared with each other and evaluated by reference to the blood shear stress.

Also preferably, (a) an ultrasonic probe which irradiates the above-described ultrasonic waves toward the above-described blood vessel is provided with a longitudinal ultrasonic detector array having a plurality of ultrasonic oscillators arranged linearly in a longitudinal direction of the above-described blood vessel, and a transverse ultrasonic detector array having a plurality of ultrasonic oscillators arranged linearly in a direction perpendicular to the longitudinal direction of the above-described blood vessel, and (b) the blood flow velocity within the above-described blood vessel is measured with the ultrasonic waves irradiated from the above-described longitudinal ultrasonic detector array, and the diameter of the above-described blood vessel is measured with the ultrasonic waves irradiated from the above-described transverse ultrasonic detector array. In this case, it is possible to implement the measurement of the above-described blood flow velocity and the measurement of the diameter of the above-described blood vessel, concurrently with each other, by using the ultrasonic probe practically used in the art. For example, the concurrent measurements of the above-described blood flow velocity and the diameter of the above-described blood vessel can be implemented by alternately operating the above-described longitudinal ultrasonic detector array and the above-described transverse ultrasonic detector array, with an extremely short cycle time.

Also preferably, (a) the ultrasonic probe which irradiates an ultrasonic waves toward the above-described blood vessel is provided with a longitudinal ultrasonic detector array having a plurality of ultrasonic oscillators arranged linearly in a longitudinal direction of the above-described blood vessel, and (b) an operation of the above-described longitudinal ultrasonic detector array to measure the blood flow velocity within the above-described blood vessel and an operation of the longitudinal ultrasonic detector array to measure the diameter of the above-described blood vessel are alternately performed with time. In this case, it is possible to implement the measurement of the above-described blood flow velocity and the measurement of the diameter of the above-described blood vessel, concurrently with each other, by using the ultrasonic probe practically used in the art. For example, the concurrent measurements of the above-described blood flow velocity and the diameter of the above-described blood vessel can be implemented by alternately operating the above-described longitudinal ultrasonic detector array and the above-described transverse ultrasonic detector array, with an extremely short cycle time.

Also preferably, the above-described predetermined condition for changing the method of arithmetic operation is a condition that the number of pulses upon said releasing of the blood vessel from the blood flow obstruction is equal to or larger than a threshold value, and this predetermined condition for changing the method of arithmetic operation is satisfied when the number of the pulses upon said releasing of the blood vessel from the blood flow obstruction is equal to or larger than said threshold value.

MODE FOR CARRYING OUT THE INVENTION

Embodiments of the present invention will be described in detail by reference to the drawings.
Embodiment 1

Figure 1:
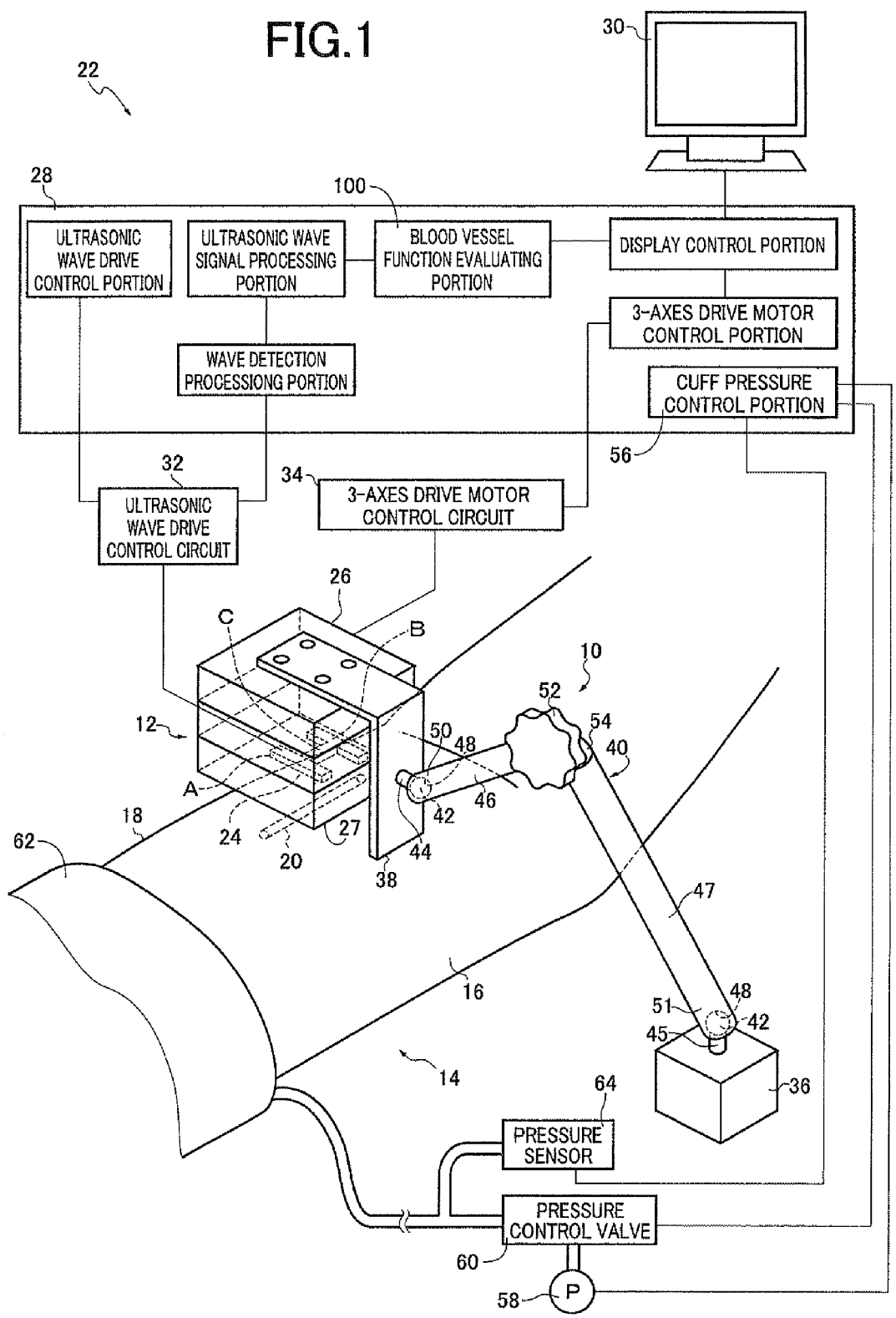
FIG. 1 is a view showing an overall arrangement of a blood vessel function inspecting apparatus according to one embodiment of this invention.

FIG. 1 is the view showing an overall arrangement of a blood vessel function inspecting apparatus 22 constructed to perform FMD (flow mediated vasodilation) evaluation (inspection) of a blood vessel 20 immediately below a skin 18 of a brachium 16 of a live body 14, by measuring a velocity of a blood flow through the blood vessel 20 and a diameter of the blood vessel 20, through the skin 18, using a hybrid probe unit 12 held by a sensor holder 10.

The hybrid probe unit 12, which functions as a sensor for detecting vital body information relating to the blood vessel 20, that is, blood vessel parameters, is provided with an H-type ultrasonic probe 24, and a multi-axes drive device (positioning device) 26 for positioning the ultrasonic probe 24. The ultrasonic probe 24 has a pair of mutually parallel detector arrays consisting of a first short-axis ultrasonic detector array A and a second short-axis ultrasonic detector array B, and a long-axis ultrasonic detector array C which connects the first and second short-axis ultrasonic arrays A and B at longitudinally intermediate portions thereof. The ultrasonic detector arrays A, B and C lie on one plane, namely, on a flat detection plane 27. Each of the first short-axis ultrasonic detector array A, second short-axis ultrasonic detector array B, and long-axis ultrasonic detector array C is an elongate member having a multiplicity of ultrasonic oscillators (vibrators) $a_1$-$a_n$ which are formed of a piezoelectric ceramic material and which are arranged linearly. It will be understood that the first short-axis ultrasonic detector array A corresponds to a transverse ultrasonic detector array according to the invention, while the long-axis ultrasonic detector array C corresponds to a longitudinal ultrasonic detector array according to the invention.

Figure 2:
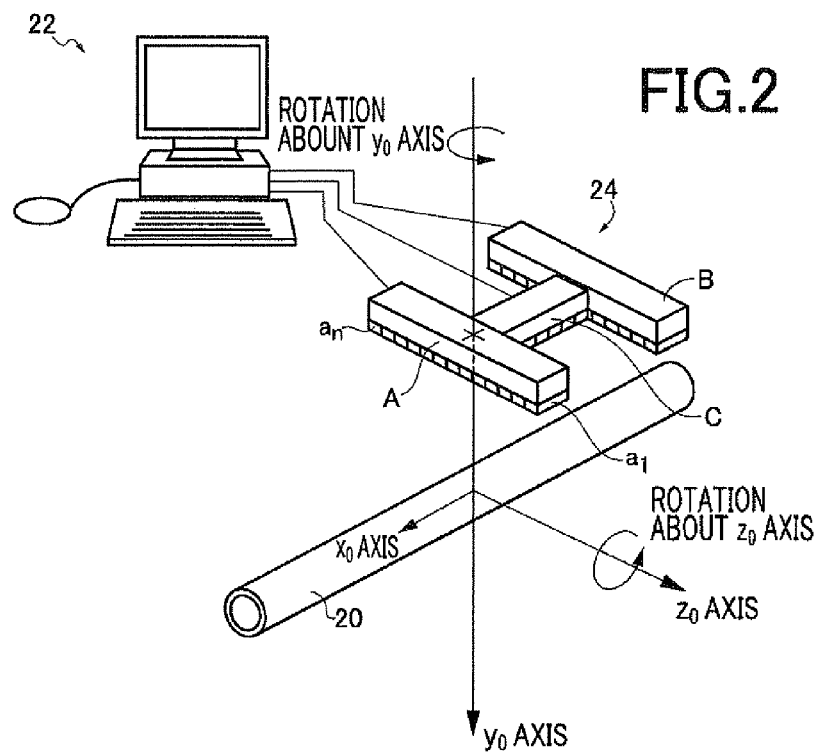
FIG. 2 is a view for explaining rectangular coordinate axes $x_0$, $y_0$ and $z_0$ for indicating an attitude of an ultrasonic probe used by the blood vessel function inspecting apparatus of FIG. 1, with respect to the blood vessel.

FIG. 2 is the view for explaining $x_0$, $y_0$ and $z_0$ axes of a rectangular coordinate system used in the present embodiment. The axis $z_0$ is parallel to the longitudinal direction of the first short-axis ultrasonic detector array A, and located right below the first short-axis ultrasonic detector array A, and passes a vertical position of the blood vessel 20 or a point vertically close to that vertical position. The $x_0$ axis is parallel to the longitudinal direction of the long-axis ultrasonic detector array C, and is perpendicular to the $z_0$ axis, while the $y_0$ axis passes a point of intersection between the longitudinal direction of the first short-axis ultrasonic detector array A and the longitudinal direction of the long-axis ultrasonic detector array C, and is perpendicular o the above-described $x_0$ and $z_0$ axes. The ultrasonic probe 24 is translated along the $x_0$ axis and rotated about the $y_0$ and $z_0$ axes by the multi-axes drive device 26.

Figure 3:
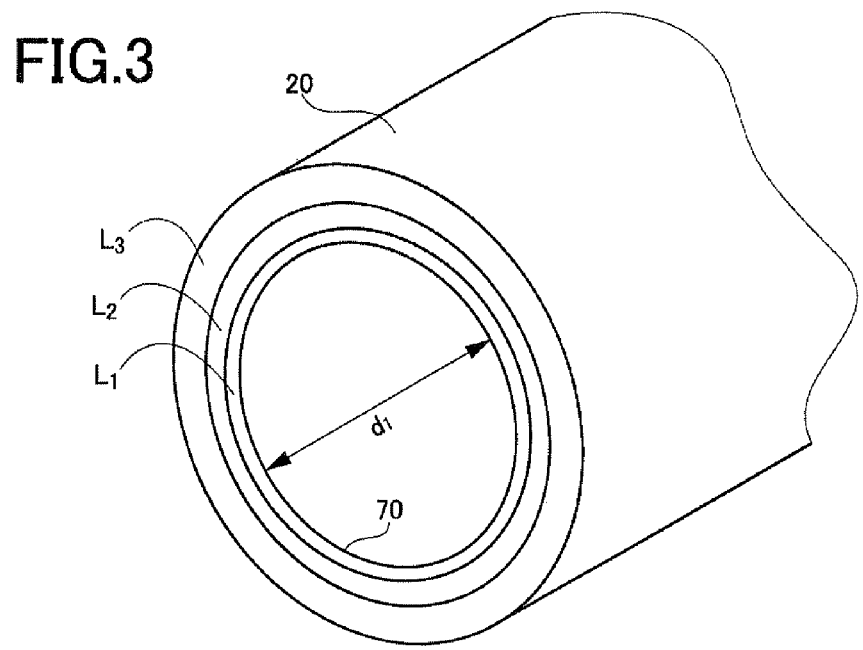
FIG. 3 is an enlarged view for explaining a multi-layered structure of the blood vessel which is a subject irradiated with an ultrasonic wave generated by the ultrasonic probe of FIG. 2.

As shown in FIG. 3, the blood vessel 20 which is a arterial vessel of the brachium, for instance, has a three-layered structure consisting of an inner layer $L_1$, an intermediate layer $L_2$ and an outer layer $L_3$. Since the reflection of an ultrasonic wave takes place in boundary portions having different values of acoustic impedance, a boundary surface between the blood in the lumen of the blood vessel and the inner layer $L_1$, and a boundary surface between the intermediate layer $L_2$ and the outer layer $L_3$ are displayed as white regions, and the tissue is displayed by white and black spots. Although the boundary surface between the blood and the inner layer $L_1$ is difficult to be displayed in an image, it is preferable to measure a distance in the image as a diameter of the blood vessel and obtain a change ratio of the diameter, namely, a dilatation ratio R of the diameter of the lumen.

Referring back to FIG. 1, the blood vessel function inspecting apparatus 22 is provided with an electronic control device 28, a monitoring image display device (image display device) 30, an ultrasonic wave drive control circuit 32, and a 3-axes drive motor control circuit 34. The electronic control device 28 is constituted by a so-called microcomputer having a CPU operable to process input signals according to programs stored in a ROM, while utilizing a temporary data storage function of a RAM. The above-described electronic control device 28 is configured to command the ultrasonic wave drive control circuit 32 to apply drive signals to the first short-axis ultrasonic detector array A, second short-axis ultrasonic detector array B and long-axis ultrasonic detector array C of the ultrasonic probe 24 of the hybrid probe unit 12, for irradiating ultrasonic waves. The irradiated ultrasonic waves are reflected as reflected ultrasonic signals, which are detected by the first and second short-axis ultrasonic detector arrays A, B and long-axis ultrasonic detector array C. The reflected ultrasonic signals are processed to generate ultrasonic images of a tissue under the skin 18, and the ultrasonic images are displayed on the monitoring image display device 30.

The monitoring image display device 30 is configured to display the ultrasonic image obtained by the first short-axis ultrasonic detector array A, the ultrasonic image obtained by the second short-axis ultrasonic detector array B, and the ultrasonic image obtained by the long-axis ultrasonic detector array C, in respective image display regions. These image display regions have a common vertical axis along which a depth dimension from the skin 18 is indicated.

The monitoring image display device 30 is further configured to chronologically display the change ratio of the diameter of the inner layer, that is, the dilatation ratio R of the lumen, for the FMD evaluation.

Upon the above-described FMD evaluation, measurement of a blood flow velocity SPD (blood flow velocity distribution DS) and generation of the ultrasonic images, the ultrasonic probe 24 is positioned in a predetermined measuring position with respect to the blood vessel 20, by the multi-axes drive device 26 which is operated according to the drive signals received from the 3-axes drive motor control circuit 34 under the control of the electronic control device 28. In the predetermined measuring position, the first short-axis ultrasonic detector array A and the second short-axis ultrasonic detector array B are perpendicular to the blood vessel 20, while the long-axis ultrasonic detector array C is parallel to the blood vessel 20. In the predetermined measuring position, the diameter of the blood vessel 20 appears in the longitudinal cross section image of the blood vessel 20 obtained by the long-axis ultrasonic detector array C.

The sensor holder 10 is constructed to hold the hybrid probe unit 12 so as to have a predetermined attitude in a predetermined position in a three-dimensional spaced, that is, in the above-described predetermined measuring position, such that the hybrid probe unit 12 is held in contact with the skin 18 of the brachium 16 of the live body 14, with a low pressure not to cause deformation of the blood vessel 20 immediately below the skin 18. Between the contact surface of the ultrasonic probe 24 of the hybrid probe unit 12 and the skin 18, there is usually interposed a well known coupling agent such as jelly, to reduce attenuation of the ultrasonic wave, and reflection and scattering of the ultrasonic wave at the boundary surfaces, for thereby obtaining clear ultrasonic images. This jelly is a gel-like water absorptive high molecular material which has a high content of aqueous components such as agar, and a sufficiently higher degree of natural impedance (sound velocity×density) than air, making it possible to reduce the attenuation of transmitted and received ultrasonic wave signals. The jelly may be replaced by a resin bag charged with water, an olive oil, or glycerin.

The above-described sensor holder 10 is provided with a magnet stand 36, unit fixture 38, connecting members 44, 45, and a universal arm 40. The magnet stand 36 is fixed with a magnetic attraction force, for example, to a desk or a pedestal, and the above-described hybrid probe unit 12 is fixed to the unit fixture 38. The connecting members 44, 45 are fixed at one end thereof to the magnet stand 36 and the unit fixture 38, respectively, and have spherical distal end portions 42. The universal arm 40 connects the magnet stand 36 and the unit fixture 38 to each other through the connecting members 44, 45 and supports the magnet stand 36 and unit fixture 38, such that the magnet stand 36 and the unit fixture 38 are movable relative to each other. The universal arm 40 has two links 46, 47 pivotably connected to each other, universal joint portions 50, 51 having respective engaging holes 48, and a pivotal joint portion 54. The engaging hole 48 is formed in one end portion of each of the two links 46, 47, and the above-described spherical distal end portion 42 is universally fitted in the engaging hole 48, with a predetermined force of resistance to universal motions of the links 46, 47 relative to the spherical distal end portion 42. The two links 46, 47 are pivotably connected to each other at the other end portions by the pivotal joint portion 54, which has a fixing knob 52 provided with an externally threaded portion screwed in tapped holes formed through the above-indicated other end portions of the links 46, 47, so that pivotal motions of the two links 46, 47 are prevented when the fixing knob 52 is tightened.

The multi-axes drive device 26 consists of a $z_0$-axis rotating (yawing) mechanism fixed to the unit fixture 38 and having a $z_0$-axis rotating actuator to rotate the ultrasonic probe 24 about the $z_0$ axis, an $x_0$-axis translating mechanism having an $x_0$-axis translating actuator to translate the ultrasonic probe 24 along the $x_0$-axis, and a $y_0$-axis rotating mechanism having a $y_0$-axis rotating actuator to rotate the ultrasonic probe 24 about the $y_0$ axis.

The ultrasonic wave drive control circuit 32 shown in FIG. 1 is commanded by the electronic control device 28 to drive the multiplicity of linearly arranged ultrasonic oscillators (vibrators) $a_1$-$a_n$ of the above-described first short-axis ultrasonic detector array A, for example, such that a group of a predetermined number of the ultrasonic oscillators, for example, a group of the 15 ultrasonic oscillators $a_1$-$a_{15}$ are concurrently driven at a frequency of about 10 MHz, with a predetermined phase difference, to implement a beam forming operation to successively irradiate ultrasonic wave beams toward the blood vessel 20, such that the ultrasonic wave beams converge in the direction of arrangement of the ultrasonic oscillators. The ultrasonic wave beams are irradiated with the members of the group of the predetermined number of the ultrasonic oscillators being shifted by one oscillator per each beam forming operation, and the thus irradiated ultrasonic wave beams are scanned to detect reflected waves, which are input to the electronic control device 28.

The electronic control device 28 synthesizes an image on the basis of the above-described reflected waves, that is, a transverse cross sectional image (short-axis image) or a longitudinal cross sectional image (long-axis image) of the blood vessel 20 below the skin 18, and display the image on the monitoring image display device (image display device) 30. Further, the electronic control device 28 calculates or measures the diameter of the blood vessel 20, or an endothelial skin diameter (blood vessel lumen diameter) $d_1$, which is a diameter of an endothelial skin 70, on the basis of the image. In addition, the electronic control device 28 calculates a dilatation ratio (change ratio) R (%) $[=100\times(d_1-d_a)/d_a]$ of the blood vessel lumen diameter (having the diameter $d_a$ at rest) of the blood vessel representative of the FMD (flow mediated vasodilation) after ischemic reaction congestion, for evaluating the function of the endothelial skin 70 of the blood vessel.

Figure 4:
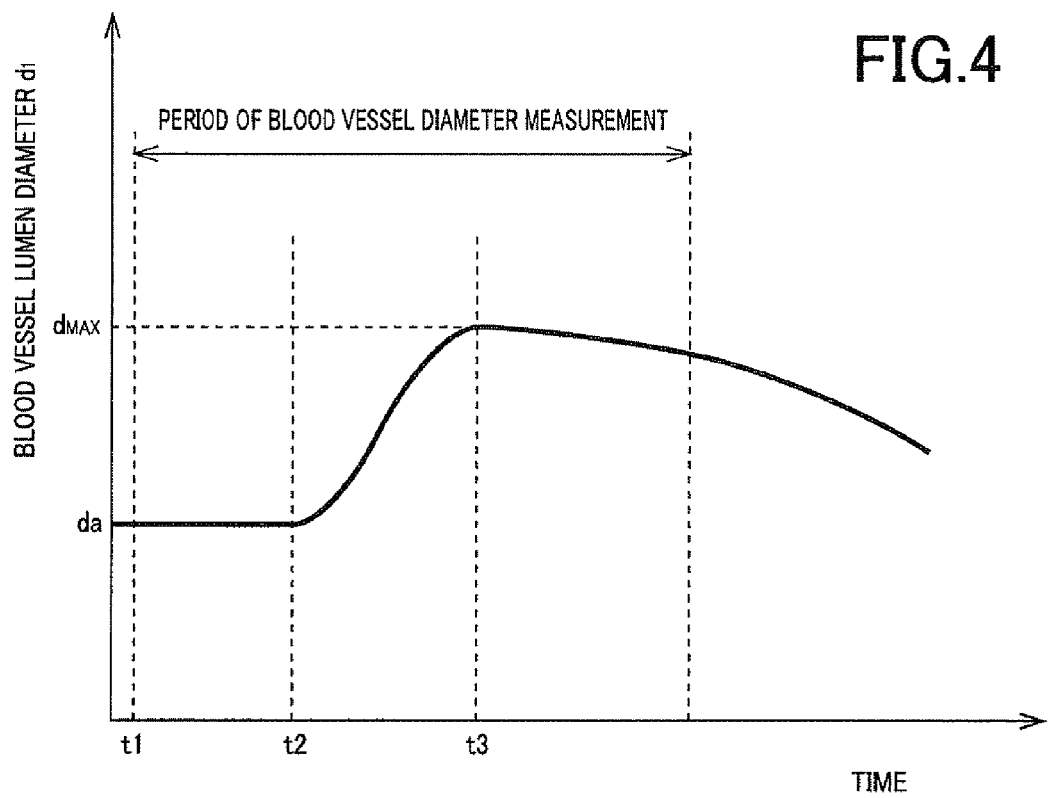
FIG. 4 is a time chart indicating an example of a change of an inside diameter of the blood vessel lumen after releasing of the blood vessel from blood flow obstruction, which is measured with the ultrasonic wave generated from the ultrasonic probe of FIG. 2.

FIG. 4 is the time chart indicating an example of a change of the blood vessel lumen diameter $d_1$ after releasing of the blood vessel from blood flow obstruction (bloodlessness). In the example of FIG. 4, the blood vessel is released from blood flow obstruction, at a point of time t1, and the blood vessel lumen diameter $d_1$ begins to increase at a point of time t2, and reaches a maximum value $d_{MAX}$ at a point of time t3. Thus, the dilatation ratio R of the blood vessel lumen diameter calculated by the electronic control device 28 is maximized at the point of time t3.

The above-described blood flow obstruction for the FMD evaluation is conducted by a cuff 62 which is wound on the brachium 16, as shown in FIG. 1, and an air pressure of which is controlled by a pressure control valve 60 under the control of a cuff pressure control portion 56 (cuff pressure control means 56) of the electronic control device 28. The pressure control valve 60 controls the pressure of pressurized air delivered from a pneumatic pump 58, so that the air pressure of the cuff (cuff pressure) 62 is raised to a predetermined blood flow obstruction value higher than the systolic blood pressure of the live body 14. The above-described cuff pressure control portion 56 detects the air pressure of the cuff 62 on the basis of an output signal of a pressure sensor 64 provided to detect the air pressure. In the example of FIG. 4, the air pressure of the cuff 62 is kept at the above-described blood flow obstruction value under the control of the cuff pressure control portion 56, for a predetermined length of time before a moment of releasing of the blood vessel from the blood flow obstruction, that is, before the point of time t1, and is abruptly lowered to the atmospheric pressure value at the point of time t1.

The above-described electronic control device 28 shown in FIG. 1 has, in addition to the above-described function, a function of measuring a velocity of flow SPD of the blood through the blood vessel 20 in a non-invasion manner, with the ultrasonic waves irradiated from the long-axis ultrasonic detector array C toward the blood vessel 20 of the live body. For instance, the electronic control device 28 measures the blood flow velocity SPD in a portion of the blood vessel 20 for which the blood vessel lumen diameter $d_1$ is measured concurrently with evaluation of the FMB. Then, the electronic control device 28 calculates a blood shear stress SS on the basis of the measured blood flow velocity SPD. For instance, the electronic control device 28 can concurrently implement the measurement of the blood vessel lumen diameter $d_1$ (dilatation ratio R of the blood vessel lumen diameter $d_1$) and the measurement of the blood flow velocity SPD, by alternately driving the first short-axis ultrasonic detector array A and the long-axis ultrasonic detector array C, with an extremely short cycle time. Alternatively, the electronic control device 28 can concurrently implement the measurement of the blood flow velocity SPD and the measurement of the blood vessel lumen diameter $d_1$, by alternately repeating an operation of the long-axis ultrasonic detector array C to measure the blood flow velocity SPD, and an operation of the same to measure the blood vessel lumen diameter $d_1$, with an extremely short cycle time, this measurement is implemented without using the first short-axis ultrasonic detector array A.

Figure 5:
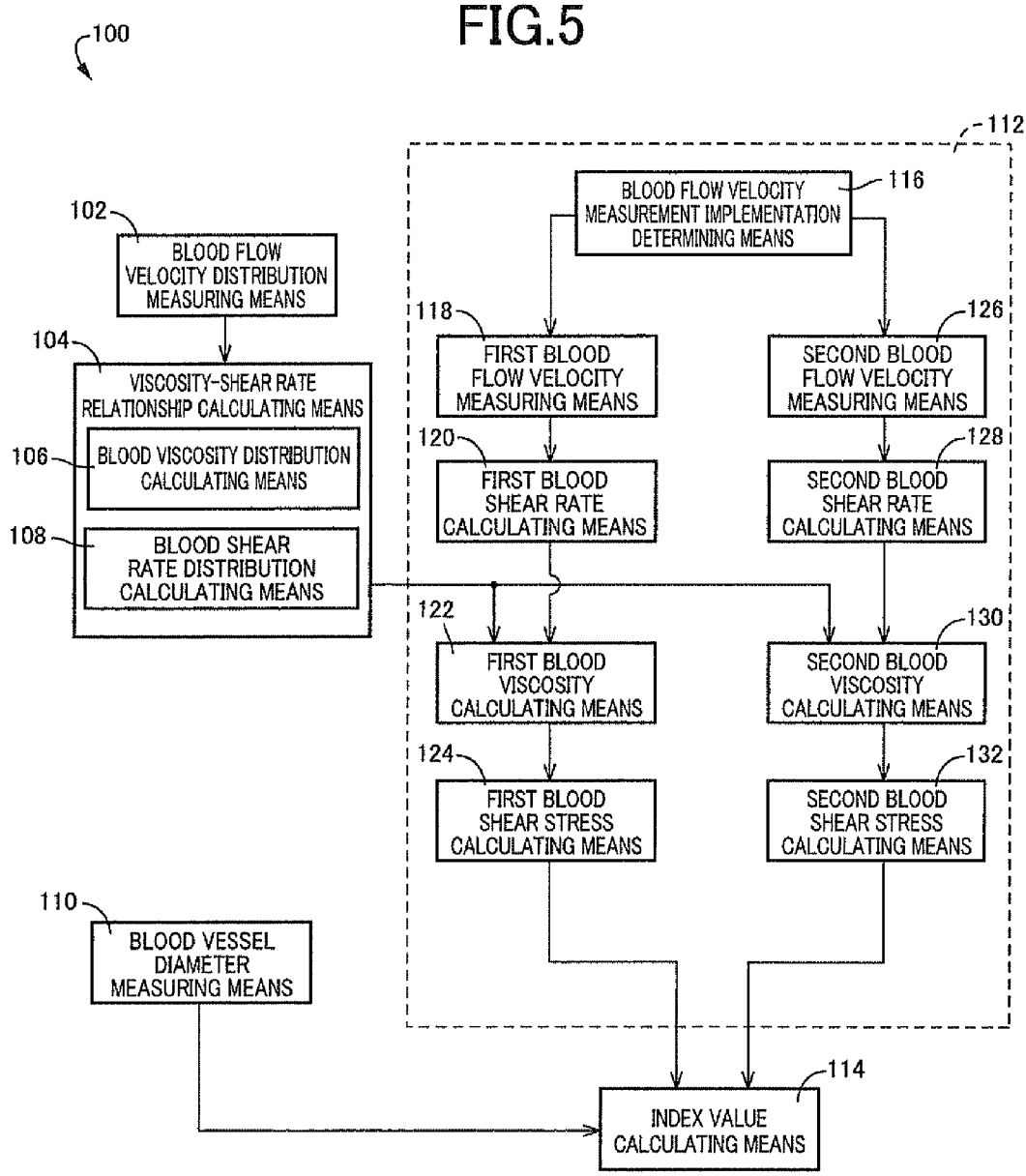
FIG. 5 is a functional block diagram for explaining major control functions of the blood vessel function inspecting apparatus of FIG. 1 according to the first embodiment.

FIG. 5 is the functional block diagram for explaining major control functions of the blood vessel function inspecting apparatus 22 (blood vessel function evaluating portion 100). As shown in FIG. 5, the blood vessel function evaluating portion 100 (shown in FIG. 1) incorporated in the electronic control device 28 is provided with a blood flow velocity distribution measuring portion in the form of blood flow velocity distribution measuring means 102, a viscosity-shear rate relationship calculating portion in the form of viscosity-shear rate relationship calculating means 104, a blood vessel diameter measuring portion in the form of blood vessel diameter measuring means 110, a blood shear stress calculating portion in the form of blood shear stress calculating means 112, and an index value calculating portion in the form of index value calculating means 114. The viscosity-shear rate relationship calculating means 104 is provided with a blood viscosity distribution calculating portion in the form of blood viscosity distribution calculating means 106, and a blood shear rate distribution calculating portion in the form of blood shear rate distribution calculating means 108. The blood shear stress calculating means 112 is provided with a blood flow velocity measurement implementation determining portion in the form of blood flow velocity measurement implementation determining means 116, a first blood flow velocity measuring portion in the form of first blood flow velocity measuring means 118, a first blood shear rate calculating portion in the form of first blood shear rate calculating means 120, a first blood viscosity calculating portion in the form of first blood viscosity calculating means 122, a first blood shear stress calculating portion in the form of first blood shear stress calculating means 124, a second blood flow velocity measuring portion in the form of second blood flow velocity measuring means 126, a second blood shear rate calculating portion in the form of second blood shear rate calculating means 128, a second blood viscosity calculating portion in the form of second blood viscosity calculating means 130, and a second blood shear stress calculating portion in the form of second blood shear stress calculating means 132.

Figure 6:
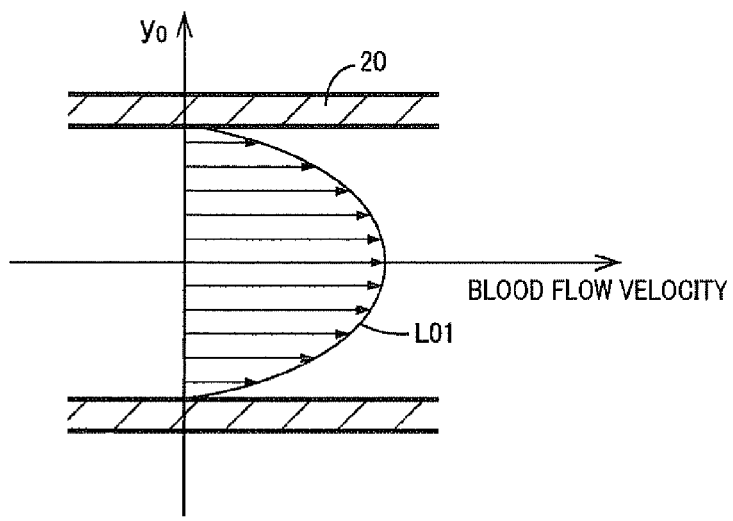
FIG. 6 is an illustrative view indicating a blood flow velocity distribution to be measured by the blood vessel function inspecting apparatus of FIG. 1.
Figure 7:
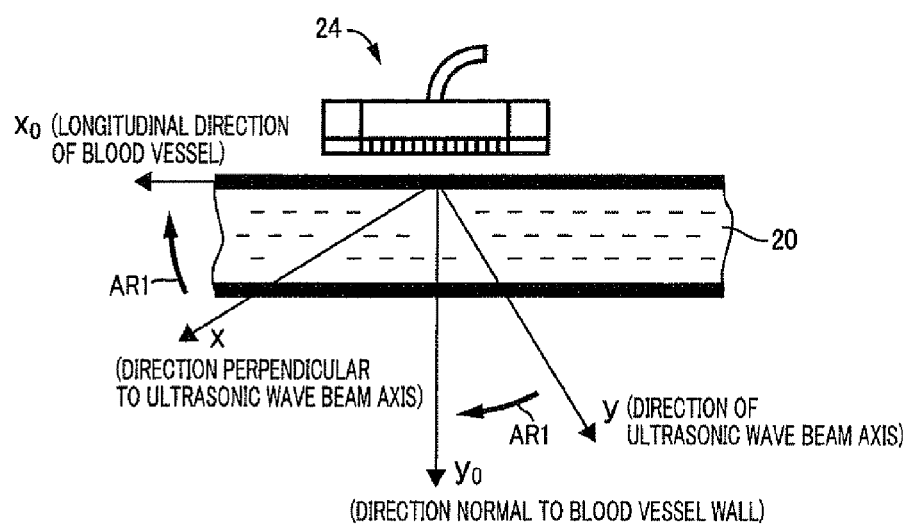
FIG. 7 is a view for explaining reference characters in an equation used for calculating the blood flow velocity distribution to be measured by the blood vessel function inspecting apparatus of FIG. 1.

The blood flow velocity distribution measuring means 102 is configured to measure the blood flow velocity distribution DS within the blood vessel 20, in a non-invasion manner with the ultrasonic wave, by utilizing the Doppler effect, prior to releasing of the blood vessel 20 from the blood flow obstruction, in the FMD evaluation. Described more specifically, the blood flow velocity distribution measuring means 102 measures the above-descried blood flow velocity distribution DS while the live body is at rest prior to the above-described releasing of the blood vessel from the blood flow obstruction. This blood flow velocity distribution DS measured at rest is referred to as a rest-time blood flow velocity distribution $DS_{RT}$. Described in detail, the rest-time blood flow velocity distribution $DS_{RT}$ is measured by the blood flow velocity distribution measuring means 102, the position of the blood vessel 20 is determined by generating a tomographic image on the basis of scattered ultrasonic waves (reflected waves; echo) received by the long-axis ultrasonic detector array C of the ultrasonic probe 24, and at the same time a two-dimensional velocity vector distribution in a two-dimensional tomographic plane is obtained. The thus obtained two-dimensional velocity vector is used as the rest-time blood flow velocity distribution $DS_{RT}$. Although the velocity vector distribution to be obtained may be either two-dimensional or three-dimensional, the two-dimensional velocity vector, distribution is obtained in the present embodiment, for simplifying the processing operation. A solid line L01 in the illustrative view of FIG. 6 represents an instantaneous blood flow velocity distribution DS (rest-time blood flow velocity distribution $DS_{RT}$). Preferably, the blood flow velocity distribution measuring means 102 is configured to chronologically measure the rest-time blood flow velocity distribution $DS_{RT}$ continuously or intermittently for a length of time corresponding to one heart beat. The above-described two-dimensional velocity vector distribution or three-dimensional velocity vector distribution can be obtained by obtaining a distance of movement of blood cells by a phase correlation method using two ultrasonic tomographic images or three-dimensional volume images (each being chronologically continuous) obtained at a predetermined time interval, and by dividing the obtained distance of movement by the time interval of the two images. Alternatively, the blood flow velocity distribution measuring means 102 can obtained a perfect two-dimensional velocity vector distribution by obtaining a velocity component in the direction of irradiation of the ultrasonic wave (which is one of velocity components of the two-dimensional velocity vector) by a method similar to a well known color Doppler method, then obtaining the other velocity component normal to the obtained one velocity component, using a incompressibility condition in the fluid dynamics as represented by the following Equation (1) stored in a memory. As described above, the blood flow velocity distribution measuring means 102 measures the rest-time blood flow velocity distribution $DS_{RT}$ within the blood vessel 20 in the non-invasion manner with the ultrasonic waves irradiated toward the blood vessel 20 in the live body 14, prior to the measurement of the diameter change ratio R of the blood vessel 20 after releasing of the blood vessel 20 from the blood flow obstruction. Needless to confirm, before the blood flow velocity distribution measuring means 102 implements the measurement of the rest-time blood flow velocity distribution $DS_{RT}$, the ultrasonic probe 24 is positioned in the above-described predetermined measuring position with respect to the blood vessel 20. As indicated in FIG. 7, "x", "y", "u" and "v" in the following Equation (1) respectively represent: a position in a direction perpendicular to the ultrasonic wave beam axis; a position in the direction of the ultrasonic wave beam axis (in the direction of irradiation of the ultrasonic wave); a velocity component in the x direction; and a velocity component in the direction of the ultrasonic wave beam axis, that is, in the y direction.

[Equation 1]

$$\frac{\partial u}{\partial x} + \frac{\partial v}{\partial y} = 0 \qquad (1)$$

The viscosity-shear rate relationship calculating means 104 is configured to calculate a viscosity-shear rate relationship VCSR prior to the blood vessel releasing from the blood flow obstruction, and prior to the measurement of the diameter change ratio R of the blood vessel 20 after the blood vessel releasing from the blood flow obstruction, on the basis of the rest-time blood velocity distribution $DS_{RT}$ measured by the blood flow velocity distribution measuring means 102. The viscosity-shear rate relationship VCSR is a relationship between a viscosity μ of the blood and a shear rate SR of the blood. The viscosity-shear rate relationship VCSR is calculated in advance to permit immediate calculation of the blood viscosity μ from the blood shear rate SR. In this respect, therefore, the relationship VCSR between the blood viscosity μ and the blood shear rate SR may be represented by an equation, or a table or graph representative of the relationship. When the viscosity-shear rate relationship calculating means 104 calculates the viscosity-shear rate relationship VCSR, the viscosity-shear rate relationship calculating means 104 first calculates a viscosity distribution DV of the blood (blood viscosity distribution DV) and a shear rate distribution DSR of the blood (blood shear rate distribution DSR) on the basis of the rest-time blood flow velocity distribution $DS_{RT}$ measured by the blood flow velocity distribution measuring means 102. Described more specifically, the blood viscosity distribution calculating means 106 and the blood shear rate distribution calculating means 108 of the viscosity-shear rate relationship calculating means 104 respectively calculate the blood viscosity distribution DV and the blood shear rate distribution DSR, in the following manners.

The blood viscosity distribution calculating means 106 is configured to calculate the viscosity distribution DV of the blood within the blood vessel 20 under measurement, on the basis of the rest-time blood flow velocity distribution $DS_{RT}$ measured by the blood flow velocity distribution measuring means 102, and according to two-dimensional Navier-Stokes equations which are stored in the memory and which are represented by the following Equations (2) and (3). This blood viscosity distribution DV calculated on the basis of the rest-time blood flow velocity distribution $DS_{RT}$ is referred to as a rest-time blood viscosity distribution $DV_{RT}$. A solid line L02 in the illustrative view of FIG. 8 indicates an example of the instantaneous blood viscosity distribution DV (rest-time blood viscosity distribution. $DV_{RT}$), which has non-Newton characteristics of the blood. Where the rest-time blood flow velocity distribution $DS_{RT}$ is a three-dimensional velocity vector distribution, the rest-time blood viscosity distribution $DV_{RT}$ is calculated according to the Navier-Stokes equations which are three-dimensional.

[Equation 2]

$$\frac{\partial u}{\partial t} + u\frac{\partial u}{\partial x} + v\frac{\partial u}{\partial y} = -\frac{1}{\rho}\frac{\partial p}{\partial x} + \nu\left(\frac{\partial^2 u}{\partial x^2} + \frac{\partial^2 u}{\partial y^2}\right) \qquad (2)$$

[Equation 3]

$$\frac{\partial v}{\partial t} + u\frac{\partial v}{\partial x} + v\frac{\partial v}{\partial y} = -\frac{1}{\rho}\frac{\partial p}{\partial y} + \nu\left(\frac{\partial^2 v}{\partial x^2} + \frac{\partial^2 v}{\partial y^2}\right) \qquad (3)$$

[Equation 4]

$$\nu = \frac{\mu}{\rho} \qquad (4)$$

[Equation 5]

$$\nu = \frac{\frac{\partial \xi}{\partial t} + u\frac{\partial \xi}{\partial x} + v\frac{\partial \xi}{\partial y}}{\frac{\partial^2 \xi}{\partial x^2} + \frac{\partial^2 \xi}{\partial y^2}} \qquad (5)$$

[Equation 6]

$$\xi = \frac{\partial u}{\partial y} - \frac{\partial v}{\partial x} \qquad (6)$$

In the above Equations (2) and (3), the reference characters "x", "y", "u" and "v" are the same as those in the above Equation (1), and "t", "p", "ρ" and "ν" respectively represent: time; pressure; density of the blood; and kinematic viscosity (coefficient of kinematic viscosity). Where the blood has the viscosity (coefficient of viscosity) μ, the kinematic viscosity ν is calculated according to the above Equation (4). Alternatively, the kinematic viscosity ν can be obtained according to the above Equation (5) which is derived by deleting the term of the pressure "p" included in the above Equations (2) and (3), by differentiation. In the Equation (5), "ξ" represents the vorticity, which is calculated according to the above Equation (6) and is defined by the velocity vector component only, as is apparent from this Equation (6).

Figure 9:
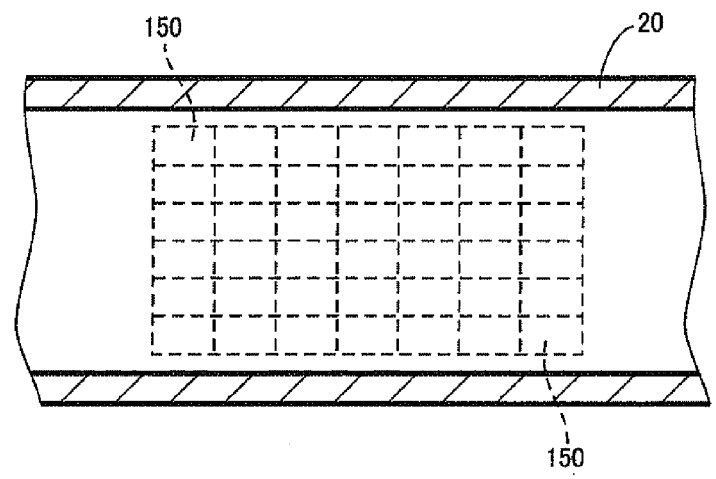
FIG. 9 is a view indicating an example of virtual division of a space within the blood vessel the blood flow velocity distribution of which is measured with the ultrasonic wave generated from the ultrasonic probe of FIG. 2, wherein the space is divided into a plurality of smaller sub-regions.

When the blood viscosity distribution calculating means 106 calculates the rest-time blood viscosity distribution $DV_{RT}$ on the basis of the rest-time blood flow velocity distribution $DS_{RT}$, the blood is presumed to be incompressible, and the space within the blood vessel 20 is virtually divided into a plurality of smaller sub-regions 150, as shown in FIG. 9. The blood viscosity distribution calculating means 106 applies the above-described Navier-Stokes equations to each of the sub-regions 150, and combines together the values of the blood viscosity μ calculated for the respective sub-regions 150, to calculate the rest-time blood viscosity distribution $DV_{RT}$.

Figure 8:
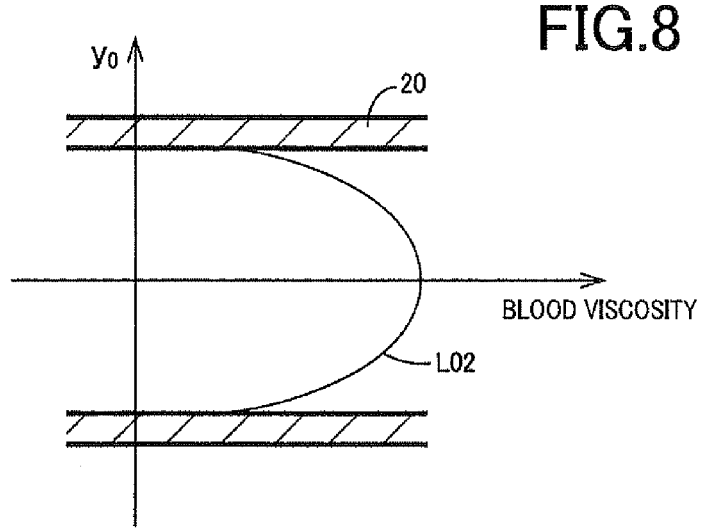
FIG. 8 is an illustrative view indicating a blood viscosity distribution calculated by the blood vessel function inspecting apparatus of FIG. 1 on the basis of the above-indicated blood flow velocity distribution.
Figure 10:
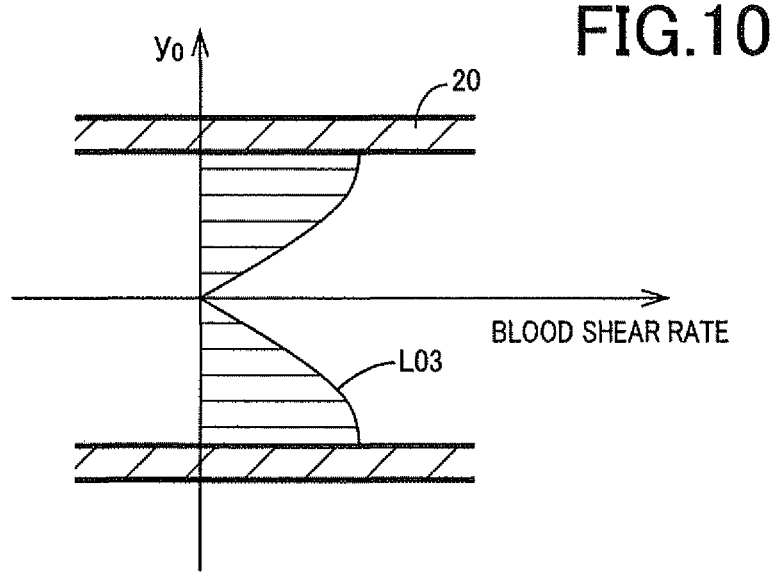
FIG. 10 is an illustrative view indicating a blood shear rate distribution calculated by the blood vessel function inspecting apparatus of FIG. 1 on the basis of the above-indicated blood flow velocity distribution.

The blood shear rate distribution calculating means 108 is configured to calculate the shear rate distribution DSR of the blood within the blood vessel 20 under measurement, on the basis of the rest-time blood flow velocity distribution $DS_{RT}$ measured by the blood flow velocity distribution calculating means 102. Described more specifically, the blood shear rate distribution calculating means 108 obtains a two-dimensional shear rate tensor on the basis of the rest-time blood flow velocity distribution $DS_{RT}$ (two-dimensional velocity vector distribution), and determines, by approximation, the normal direction of the blood vessel 20 to be a direction normal to a line of the blood flow a direction of tangency of which is parallel to the direction of the two-dimensional velocity vector. The blood shear rate distribution calculating means 108 obtains a shear component $e_{xy0}$ by rotatory coordinate conversion (indicated by arrow-headed lines AR1 in FIG. 7) of the above-described two-dimensional shear rate component with respect to the normal direction of the blood vessel 20 determined by approximation as described above, and extracts the shear component $e_{xy0}$ as the blood shear rate SR, to calculate the blood shear rate distribution DSR. The blood shear rate distribution DSR calculated on the basis of the rest-time blood flow velocity distribution $DS_{RT}$ is referred to as a rest-time blood shear rate distribution $DSR_{RT}$. A solid line L03 in the illustrative view of FIG. 10 indicates an example of the instantaneous blood shear rate distribution DSR (rest-time blood shear rate distribution $DSR_{RT}$). It is noted that the above-described shear component $e_{xy0}$ is represented by the following Equation (7), which is stored in the blood shear rate distribution calculating means 108. Where the rest-time blood flow velocity distribution $DS_{RT}$ is a three-dimensional velocity vector distribution, the rest-time blood shear rate distribution $DSR_{RT}$ is calculated according to the above-described shear rate tensor which is three-dimensional. The values $x_0$, $y_0$, $u_0$ and $v_0$ in the following Equation (7) are obtained by rotatory coordinate conversion (indicated by the arrow-headed lines AR1 in FIG. 7) of the values x, y, u and v in the above Equation (1), and the $y_0$ axis coincides with the direction normal to the blood vessel wall, and the $x_0$ axis coincides with the longitudinal direction of the blood vessel 20, as indicated in FIGS. 2 and 7. Further, the y axis coincides with the direction of the ultrasonic wave beam axis, and the x axis coincides with the direction perpendicular to the ultrasonic wave beam axis. The character "$u_0$" represents the velocity component in the $x_0$ direction, and the reference character "$v_0$" represents the velocity component in the $y_0$ direction. FIGS. 6, 8 and 10 referred to above are illustrative views, which are not necessarily coincident with the views of the actual distributions. The rest-time blood shear rate distribution $DSR_{RT}$ indicated in FIG. 10 is based on absolute coordinate values obtained as a result of processing of the rest-time blood flow velocity distribution $DS_{RT}$ according to a difference equation.

[Equation 7]

$$e_{xy0} = \frac{1}{2}\left(\frac{\partial u_0}{\partial y_0} + \frac{\partial v_0}{\partial x_0}\right) \quad (7)$$

When the blood shear rate distribution calculating means 108 calculates the rest-time blood shear rate distribution $DSR_{RT}$ on the basis of the rest-time blood flow velocity distribution $DS_{RT}$, the space within the blood vessel 20 is virtually divided into the plurality of smaller sub-regions 150, as shown in FIG. 9, as in the calculation of the rest-time blood viscosity distribution $DV_{RT}$, and the blood shear rate distribution calculating means 108 applies the above-indicated Equation (7) to each of the sub-regions 150, and combines together the values of the blood viscosity μ calculated for the respective sub-regions 150, to calculate the shear component $e_{xy0}$ as the blood shear rate SR for each sub-region 150. The blood shear rate distribution calculating means 108 calculates the rest-time blood shear rate distribution $DSR_{RT}$ by combining the values of the blood shear rate SR ($e_{xy0}$) calculated for the respective sub-regions 150.

After the blood viscosity distribution calculating means 106 and the blood shear rate distribution calculating means 108 have calculated the rest-time blood viscosity distribution $DV_{RT}$ and the rest-time blood shear rate distribution $DSR_{RT}$, respectively, the viscosity-shear rate relationship calculating means 104 calculates the viscosity-shear rate relationship VCSR, on the basis of values of the blood viscosity μ and values of the blood shear rate SR, which values are extracted from the calculated rest-time blood viscosity distribution $DV_{RT}$ and rest-time blood shear rate distribution $DSR_{RT}$, respectively, and which respectively correspond to a plurality of predetermined points within the blood vessel 20. Described more specifically, the viscosity-shear rate relationship calculating means 104 calculates the viscosity-shear rate relationship VCSR on the basis of the extracted values of the blood viscosity μ and blood shear rate SR, in the following manner.

The viscosity-shear rate relationship calculating means 104 stores therein a plurality of predetermined points, namely, a plurality of sampling points within the blood vessel 20 under measurement, for extracting a plurality of sets of values of the blood viscosity μ and blood shear rate SR from the calculated rest-time blood viscosity distribution $DV_{RT}$ and rest-time blood shear rate distribution $DSR_{RT}$. These plural sampling points are arbitrarily selected within an area of the blood vessel 20 for which the rest-time blood viscosity distribution $DV_{RT}$ and rest-time blood shear rate distribution $DSR_{RT}$ have been calculated. The viscosity-shear rate relationship calculating means 104 extracts the values of the blood viscosity μ corresponding to the respective sampling points, from the rest-time blood viscosity distribution $DV_{RT}$, and the values of the blood shear rate SR corresponding to the respective sampling points, from the rest-time blood shear rate distribution $DSR_{RT}$. The values of each extracted set of the blood viscosity μ and blood shear rate SR are coincident with each other in the spatial position within the blood vessel 20, being extracted at the corresponding one of the sampling points. Where the rest-time blood viscosity distribution $DV_{RT}$ and rest-time blood shear rate distribution $DSR_{RT}$ are not obtained instantaneously, but are obtained continuously or intermittently, the above-indicated values of each set are also chronologically coincident with each other.

After the extraction of the sets of values of the blood viscosity μ and blood shear rate SR at the above-descried plurality of sampling points, the viscosity-shear rate relationship calculating means 104 calculates one viscosity-shear rate relationship VCSR representative of the relationship between the extracted blood viscosity μ and blood shear rate SR or a relationship approximate to that relationship. This viscosity-shear rate relationship VSCR is calculated as a curve (viscosity-shear rate relationship curve) which connects relationship points indicative of the values of the blood viscosity μ and blood shear rate SR at the above-described sampling points in the coordinate system in which the blood viscosity μ and blood shear rate SR are taken as parameters.

Alternatively, the viscosity-shear rate relationship VCSR is calculated as an equation of relationship (viscosity-shear rate relationship equation) representative of the viscosity-shear rate relationship curve and the relationship between the blood viscosity μ and blood shear rate SR. Where the relationship points indicative of the values of the blood viscosity μ and blood shear rate SR (viscosity-shear rate relationship points) at the above-described sampling points cannot be connected to each other by one curve, the above-described viscosity-shear rate relationship VCSR is calculated by approximation using the method of least squares. Described more specifically, the above-described viscosity-shear rate relationship curve is represented by an approximation curve which connects points approximate to the above-described viscosity-shear rate relationship points at the above-described plurality of sampling points, and the above-described viscosity-shear rate relationship equation is an equation of relationship representative of the approximation curve (viscosity-shear rate relationship curve) and the relationship between the blood viscosity μ and blood shear rate SR. The calculation of this viscosity-shear rate relationship VCSR will be described by reference to FIG. 11.

Figure 11:
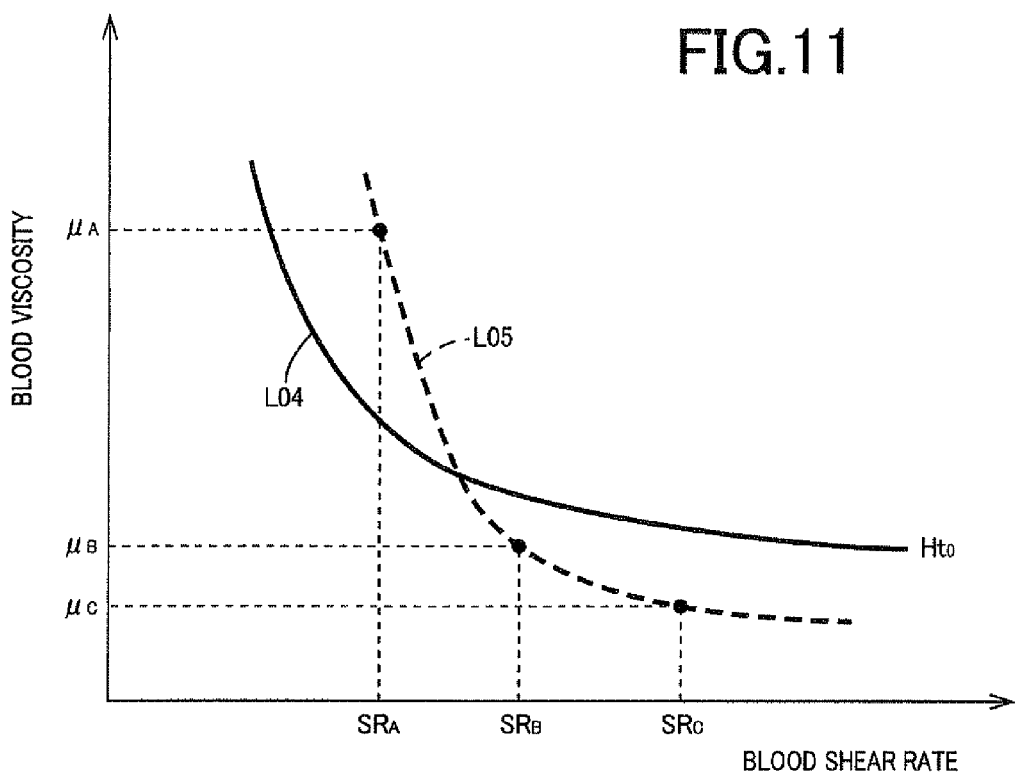
FIG. 11 is a view indicating examples of a relationship between a blood viscosity and a blood shear rate extracted from the above-indicated blood viscosity distribution and blood shear rate distribution by the blood vessel function inspecting apparatus of FIG. 1.

FIG. 11 is the view indicating examples of the above-described viscosity-shear rate relationship curve representing the relationship between the blood viscosity μ and the blood shear rate SR extracted from the rest-time blood viscosity distribution $DV_{RT}$ and the rest-time blood shear rate distribution $DSR_{RT}$. In the case of FIG. 11, three sets of the values of the blood viscosity μ and the blood shear rate SR are extracted. A solid line L04 represents the relationship between the blood viscosity μ and the blood shear rate SR of a healthy subject person whose blood is normal having a normal hematocrit value $Ht_0$ (normal value).

The three sets of the blood viscosity μ and the blood shear rate SR are extracted at the respective three sampling points in the case of FIG. 11. In the first sampling point $P_A$, the blood viscosity value $\mu_A$ and the blood shear rate value $SR_A$ are extracted. In the second sampling point $P_B$, the blood viscosity value $\mu_B$ and the blood shear rate value $SR_B$ are extracted. In the third sampling point $P_C$, the blood viscosity value $\mu_C$ and the blood shear rate value $SR_C$ are extracted. When the above-described blood viscosity values $\mu_A$, $\mu_B$, and $\mu_C$, and the above-described blood shear rate values $SR_A$, $SR_B$ and $SR_C$ are indicated in FIG. 11, a relationship represented by a broken line L05 is obtained, for example. In the case of FIG. 11, this broken line L05 is the above-described viscosity-shear rate relationship line based on the relationship between the blood viscosity μ and the blood shear rate SR at each of the above-described plurality of sampling points. Namely, the relationship between the blood viscosity μ and the blood shear rate SR, which is represented by this broken line L05, is the above-described viscosity-shear rate relationship VCSR.

When the viscosity-shear rate relationship calculating means 104 calculates the viscosity-shear rate relationship VCSR as the above-described viscosity-shear rate relationship equation, the viscosity-shear rate relationship calculating means 104 obtains constants "A" and "α" in the following Equation (8) representative of the viscosity-shear rate relationship VCSR (broken line L05), for example, on the basis of the relationships between the sets of values of the blood viscosity μ and the blood shear rate SR at the respective sampling points, so that the viscosity-shear rate relationship VCSR is calculated.

[Equation 8]

$$\mu = A \cdot e^{-\alpha \cdot SR} \tag{8}$$

The blood diameter measuring means 110 is configured to synthesize an image on the basis of the ultrasonic waves irradiated by the first short-axis ultrasonic detector array A of the ultrasonic probe 24 toward the blood vessel 20 within the vital body 14, and to measure the blood vessel lumen diameter $d_1$. Described more specifically, the blood vessel diameter measuring means 110 measures and stores the blood vessel lumen diameter $d_a$ (rest-time diameter $d_a$) before releasing of the blood vessel 20 from the blood flow obstruction, for measuring the diameter change ratio of the blood vessel 20 (dilatation ration R of the blood vessel lumen diameter $d_1$) after releasing of the blood vessel 20 from the blood flow obstruction, for implementing the FMD evaluation. The blood vessel diameter measuring means 110 is further configured to measure the blood vessel lumen diameter $d_1$ during a predetermined blood vessel diameter measuring time period TIME1 after releasing of the blood vessel 20 from the blood flow obstruction, and to calculate and measure the diameter change ratio R of the blood vessel 20 on the basis of the measured blood vessel lumen diameter $d_1$ and the above-described rest-time diameter $d_a$, for implementing the FMD evaluation. For instance, the blood vessel diameter measuring means 110 chronologically continuously measures the blood vessel lumen diameter $d_1$ during the above-described blood vessel diameter measuring time period TIME1 while the blood vessel lumen diameter $d_1$ varies after releasing of the blood vessel from the blood flow obstruction, as indicated in FIG. 4. Alternatively, the blood vessel diameter measuring means 110 may measure the blood vessel lumen diameter $d_1$ at one, two or more predetermined measuring point or points of time with respect to the moment of releasing of the blood vessel from the blood flow obstruction. Each predetermined measuring point of time is a point at which the blood vessel lumen diameter $d_1$ is estimated to have the largest value $d_{MAX}$, and is obtained in advance by experimentation. The above-described blood vessel diameter measuring time period TIME1 during which the blood vessel lumen diameter $d_1$ is to be measured to detect its largest value after releasing of the blood vessel from the blood flow obstruction is determined by experimentation with respect to the moment of releasing of the blood vessel from the blood flow obstruction, and is stored in the blood vessel diameter measuring means 110. As indicated in FIG. 4, this time period TIME1 includes the point of time (t3) at which the blood vessel lumen diameter $d_1$ reaches the largest value $d_{MAX}$ and starts from the moment (point of time t1) at which the blood vessel is released from the blood flow obstruction.

In the present embodiment, the viscosity-shear rate relationship VCSR is calculated in advance of releasing of the blood vessel from the blood flow obstruction, and the blood shear stress SS is calculated on the basis of the blood flow velocity SPD by real-time processing of the blood flow velocity SPD, and according to the viscosity-shear rate relationship VCSR, after releasing of the blood vessel from the blood flow obstruction. This aspect will be described.

The blood shear stress calculating means 112 is configured to measure the velocity SPD of the blood flow through the blood vessel 20 within the above-described blood vessel diameter measuring time period TIME1 after releasing of the blood vessel 20 from the blood flow obstruction, and to calculate the blood shear stress SS on the basis of the measured blood flow velocity SPD, and according to the above-described viscosity-shear rate relationship VCSR. The operations from the step of measuring the blood flow velocity SPD through the step of calculating the blood shear stress SS are performed concurrently with the operation of the blood vessel diameter measuring means 110 to measure the diameter change ratio (dilatation ratio R of the blood vessel lumen diameter $d_1$). Described more specifically, the blood shear stress SS is calculated in the real-time processing fashion, as described below.

The blood flow velocity measurement implementation determining means 112 is configured to determine which one of the first blood flow velocity measuring means 118 and the second blood flow velocity measuring means 126 of the blood shear stress calculating means 112 that are provided as the blood flow velocity measuring means for measuring the blood flow velocity SPD should be operated to measure the blood flow velocity SPD. The blood flow velocity implementation determining means 116 determines whether a predetermined condition for changing a method of arithmetic operation is satisfied or not. This condition for changing the method of arithmetic operation is a condition which is used for determining which one of the first blood flow velocity measuring means 118 and second blood flow velocity measuring means 126 should be operated to measure the blood flow velocity SPD, and which is used for estimating the load of the arithmetic operation to calculate the blood shear stress SS after releasing of the blood vessel from the blood flow obstruction, in view of a high possibility that the load of the arithmetic operation after the measurement of the blood flow velocity SPD is higher when the blood flow velocity SPD is measured by the second blood flow velocity measuring means 126 than when it is measured by the first blood flow velocity measuring portion 118. Described more specifically, the condition for changing the method of arithmetic operation in the present embodiment is provided to determine whether the number PR of the heart beat pulses upon releasing of the blood vessel from the blood flow obstruction (release-time pulse number PR) is equal to or larger than a predetermined threshold value PR1. Namely, the condition for changing the method of arithmetic operation is satisfied when the above-described release-time pulse number PR is equal to or larger than the above-described threshold value PR1. That is, the blood flow velocity measurement implementation determining means 116 determines that the above-described condition for changing the method of arithmetic operation is satisfied when the above-described release-time pulse number PR is equal to or larger than the above-described threshold value PR1, and that the condition is not satisfied when the release-time pulse number PR is smaller than the threshold value PR1. An amount of change of the blood flow velocity SPD after releasing of the blood vessel from the blood flow obstruction increases with an increase of the release-time pulse number PR, and the load of the arithmetic operation to calculate the blood shear stress SS from the blood flow velocity SPD is considered to increase with the increase of the release-time pulse number PR. In this sense, the release-time pulse number PR is employed as an index value for the condition for changing the method of arithmetic operation. Accordingly, the above-described threshold value PR1 is a value used for determining the estimated load of arithmetic operation after releasing of the blood vessel from the blood flow obstruction. Preferably, the above-described release-time pulse number PR is measured at a point of time immediately before, that is, a predetermined short time before the moment of releasing of the blood vessel from the blood flow obstruction, to permit the measurement of the blood flow velocity SPD immediately after the moment of releasing of the blood vessel, in view of the length of time required to make the measurement and determination of the release-time pulse number PR. For example, the release-time pulse number PR is measured the above-described predetermined short time before the moment of generation of a control signal from the cuff pressure control portion 56 to lower the above-described cuff pressure to the atmospheric pressure for releasing the blood vessel from the blood flow obstruction. The pulse number of the vital body 14 can be detected by a pulse meter or an electrocardiograph, for instance.

The first blood flow velocity measuring means 118 is configured to measure an average blood flow velocity $SPD_{AVG}$ (=blood flow rate/transverse cross sectional area of the blood vessel) in the vessel 20 in a non-invasion manner within the above-described blood vessel diameter measuring time period TIME1 after releasing of the blood vessel from the blood flow obstruction, concurrently with the measurement of the diameter change rate R of the blood vessel 20 by the blood vessel diameter measuring means 110, if the blood flow velocity measurement implementation determining means 110 determines that the release-time pulse number PR is equal to or larger than the threshold value PR1. For instance, the first blood flow velocity measuring means 118 chronologically measures the average blood flow velocity $SPD_{AVG}$ continuously or at a predetermined time interval during the blood vessel diameter measuring time period TIME1 immediately after the moment of releasing of the blood vessel from the blood flow obstruction, until the time period TIME1 expires. Described more specifically, the first blood flow velocity measuring means 118 measures the blood flow velocity distribution DS in the same manner as the blood flow velocity distribution measuring means 102, and calculates and measures the average blood flow velocity $SPD_{AVG}$ from the measured blood flow velocity distribution DS. The first blood flow velocity measuring means 118 then chronologically stores in a memory device the values of the average blood flow velocity $SPD_{AVG}$ measured after releasing of the blood vessel. For example, the first blood flow velocity measuring means 118 calculates the average blood flow velocity $SPD_{AVG}$ by integrating the values of the blood flow velocity SPD within the blood flow velocity distribution DS, over the entire transverse cross sectional area of the blood vessel, and dividing a result of the integration by the transverse cross sectional area, or by multiplying the values of the blood flow velocity SPD in a specified region of the transverse cross sectional area (for instance, in a transversely central region), by a coefficient of compensation obtained by experimentation in advance. Although the average blood flow velocity $SPD_{AVG}$ measured by the first blood flow velocity measuring means 118 may be an average value (instantaneous average value) of the blood flow velocity SPD obtained by the instantaneous blood flow velocity distribution DS, the average blood flow velocity $SPD_{AVG}$ measured in the present embodiment is an average value of instantaneous average values of the blood flow velocity SPD that are obtained during a period of one heart beat. Accordingly, the first blood flow velocity measuring means 118 outputs results of measurement of the average blood flow velocity $SPD_{AVG}$ for each of the heart beats, in other words, measures the average blood flow velocity $SPD_{AVG}$ for each of the heart beats.

The first blood shear rate calculating means 120 is configured to calculate the blood shear rate SR on the basis of the average blood flow velocity $SPD_{AVG}$ measured by the first blood flow velocity measuring means 118. The first blood shear rate calculating means 120 calculates the blood shear rate SR by real-time processing of the average blood flow velocity $SPD_{AVG}$ being measured by the first blood flow velocity measuring means 118. While the method of calculating the blood shear rate SR is not particularly limited, the first blood shear rate calculating means 120 in the present embodiment calculates the blood shear rate SR by dividing the average blood flow velocity $SPD_{AVG}$ by the blood vessel diameter (for instance, blood vessel lumen diameter $d_1$), as indicated by the following Equation (9). The blood vessel lumen diameter $d_1$ used to calculate the above-described blood shear rate SR is measured by the blood vessel diameter measuring means 110 concurrently with the measurement of the above-described average blood flow velocity $SPD_{AVG}$ from which the blood shear rate SR is calculated. Although the actual blood vessel lumen diameter $d_1$ varies during the period of each heart beat, a value of the blood vessel diameter $d_1$ under a predetermined condition may be used. For instance, an average value or the largest value of the blood vessel diameter $d_1$ during the period of each heart beat may be used.

[Equation 9]

$$\text{Blood Shear rate } SR = 8 \times \frac{\text{Average Blood FlowVelocity } SPD_{AVG}}{\text{Blood VesselLumen Diameter } d_1} \quad (9)$$

The first blood viscosity calculating means 122 is configured to calculate the blood viscosity μ on the basis of the blood shear rate SR calculated by the first blood shear rate calculating means 120, and according to the viscosity-shear rate relationship VCSR calculated by the viscosity-shear rate relationship calculating means 104 prior to releasing of the blood vessel from the blood flow obstruction. The first blood viscosity calculating means 122 calculates the blood viscosity μ each time the first blood shear rate calculating means 120 calculates the blood shear rate SR, namely, in a real-time processing fashion concurrently with the measurement of the average blood flow velocity $SPD_{AVG}$ by the first blood flow velocity measuring means 118.

The first blood shear stress calculating means 124 is configured to calculate the blood shear stress SS on the basis of the blood shear rate SR calculated by the first blood shear rate calculating means 120 and the blood viscosity μ calculated by the first blood viscosity calculating means 122. Described more specifically, the first blood shear stress calculating means 124 calculates the blood shear stress SS on the basis of the blood shear rate SR and blood viscosity μ measured as described above, and according to the Newton's law of viscosity which is represented by the following Equation (10) and which is stored in memory. The first blood shear stress calculating means 124 calculates the blood shear stress SS each time the first blood shear rate calculating means 120 calculates the blood shear rate SR and the first blood viscosity calculating means 122 calculates the blood viscosity μ, namely, in a real-time processing fashion concurrently with the measurement of the average blood flow velocity $SPD_{AVG}$ by the first blood flow velocity measuring means 118. In other words, the first blood shear stress calculating means 124 calculates the blood shear stress SS for each heart beat within the above-described blood vessel diameter measuring time period TIME1, since the first blood flow velocity measuring means 118 outputs the result of measurement of the average blood flow velocity $SPD_{AVG}$ for each heart beat. The blood shear stress SS to be calculated by the first blood shear stress calculating means 124, which is an amount of state which varies even within a time period of one heart beat, is based on the average blood flow velocity $SPD_{AVG}$ measured as an average of the values of the blood flow velocity SPD within the period of each heart beat. In this respect, the blood shear stress SS can be the above-described to be a one-beat average shear stress $SS_{AVG}$ which is obtained by chronologically averaging the values of the blood shear stress SS for each heart beat. The first blood shear stress calculating means 124 commands the monitoring image display device 30 to display the blood shear stress SS immediately after and each time the blood shear stress SS is calculated as described above, for example.

[Equation 10]

$$(\text{Blood shear stress})=(\text{Blood Viscosity})\times(\text{Blood Shear rate}) \quad (10)$$

The second blood flow velocity measuring means 126 is configured to measure the blood flow velocity distribution DS within the blood vessel 20 in a non-invasion manner within the above-described blood vessel diameter measuring time period TIME1 after releasing of the blood vessel 20 from the blood flow obstruction, concurrently with the measurement of the diameter change rate R of the blood vessel 20 by the blood vessel diameter measuring means 110, if the blood flow velocity measurement implementation determining means 116 determines that the release-time pulse number PR is smaller than the threshold value PR1. The second blood flow velocity measuring means 126 then chronologically stores in a memory device the values of the blood flow velocity distribution DS measured after releasing of the blood vessel. This blood flow velocity distribution DS measured after releasing of the blood vessel is referred to as a post-release blood flow velocity distribution DS2. For instance, the second blow flow velocity measuring means 126 measures chronologically continuously the post-release blood flow velocity distribution DS2 immediately after releasing of the blood vessel, and until the blood vessel diameter measuring time period TIME1 expires. Described more specifically, the second blood flow velocity measuring means 126 measures the post-release blood flow velocity distribution DS2 in the same manner as the blood flow velocity distribution measuring means 102.

The second blood shear rate calculating means 128 is configured to calculate a maximum value $SR2_{MAX}$ of the blood shear rate SR on the basis of the post-release blood flow velocity distribution DS2 measured by the second blood flow velocity measuring means 126. Described more specifically, the second blood shear rate calculating means 128 calculates the blood shear rate distribution DSR on the basis of the post-release blood flow velocity distribution DS2 in the same manner as the blood shear rate calculating means 108, and extracts the maximum value $SR2_{MAX}$ of the blood shear rate SR from the calculated blood shear rate distribution DSR. Since the blood shear rate SR is considered to be highest at positions close to the wall of the blood vessel 20, the value of the blood shear rate SR at a predetermined position close to the blood vessel wall within the blood shear rate distribution DSR is extracted as the maximum value $SR2_{MAX}$, for example. The second blood shear rate calculating means 128 is further configured to calculate the maximum value $SR2_{MAX}$ of the blood shear rate SR, in a real-time processing fashion concurrently with the measurement of the post-release blood flow velocity distribution DS2 by the second blood flow velocity measuring means 126.

The second blood viscosity calculating means 130 is configured to calculate the blood viscosity μ on the basis of the maximum value $SR2_{MAX}$ of the blood shear rate SR calculated by the second blood shear rate calculating means 128, and according to the above-described viscosity-shear rate relationship VCSR calculated by the blood viscosity-shear rate relationship calculating means 104 in advance of the blood vessel releasing from the blood flow obstruction. The second blood viscosity calculating means 130 calculates the blood viscosity μ in a real-time processing fashion concurrently with the calculation of the above-described maximum value $SR2_{MAX}$ of the blood shear rate SR by the second blood shear rate calculating means 128. Namely, the second blood viscosity calculating means 130 calculates the blood viscosity μ in a real-time fashion concurrently with the measurement of the post-release blood flow velocity distribution DS2 by the second blood flow velocity measuring means 126.

The second blood shear stress calculating means 132 is configured to calculate the blood shear stress SS within the above-described blood vessel diameter measuring time period TIME1, on the basis of the maximum value $SR2_{MAX}$ of the blood shear rate SR calculated by the second blood shear rate calculating means 128, and the blood viscosity μ calculated by the second blood viscosity calculating means 130. Described more specifically, the second blood shear stress calculating means 132 stores the Newton's law of viscosity represented by the above-indicated Equation (10), and calculates the blood shear stress SS on the basis of the calculated maximum value $SR2_{MAX}$ of the blood shear rate SR and the calculated blood viscosity and according to the Newton's law of viscosity. The second blood shear stress calculating means 132 calculates the blood shear stress SS in a real-time processing fashion concurrently with the calculation of the above-described maximum value $SR2_{MAX}$ of the blood shear rate SR by the second blood shear rate calculating means 128 and the calculation of the above-described blood viscosity μ by the second blood viscosity calculating means 130. Namely, the second blood shear stress calculating means 132 calculates the blood shear stress SS in a real-time processing fashion concurrently with the measurement of the post-release blood flow velocity distribution DS2 by the second blood flow velocity measuring means 126. For example, the second blood shear stress calculating means 132 continuously calculates the blood shear stress SS concurrently with the continuous measurement of the post-release blood flow velocity distribution DS2 by the second blood flow velocity measuring means 126. The second blood shear stress calculating means 132 commands the monitoring image display device 30 to display the blood shear stress SS immediately after and each time the blood shear stress SS is calculated as described above, for example.

It is noted here that the post-release blood flow velocity distribution DS2 used to calculate the above-described blood shear stress SS is an instantaneous one, so that the blood shear stress SS is instantaneous like the post-release blood flow velocity distribution DS2. In view of this fact, the second blood shear stress calculating means 132 is configured to average the calculated values of the blood shear stress SS for each hear beat, and to calculate the averaged value for each heart beat, as a one-beat average shear stress $SS_{AVG}$. For instance, the second blood shear stress calculating means 132 plots the values of the blood shear stress SS within the time period of each heart beat, implements the time integration of the plotted values, and calculates the one-beat average shear stress $SS_{AVG}$ by dividing the obtained integrated value by the above-described time period of each heat beat. The second blood shear stress calculating means 132 calculates this one-beat average shear stress $SS_{AVG}$ in a real-time processing fashion concurrently with the measurement of the post-release blood velocity distribution DS2 by the second blood flow velocity measuring means 126, for each heart beat within the above-described blood vessel diameter measuring time period TIME1. The second blood shear stress calculating means 132 commands the monitoring image display device 30 to display the one-beat average shear stress $SS_{AVG}$ immediately after and each time the one-beat average shear stress $SS_{AVG}$ is calculated as described above, for example. To distinguish the one-beat average shear stress $SS_{AVG}$ calculated by the above-described first blood shear stress calculating means 124 and the one-beat average shear stress $SS_{AVG}$ calculated by the above-described second blood shear stress calculating means 132, from each other, the one-beat average shear stress $SS_{AVG}$ calculated by the first blood shear stress calculating means 124 is represented by $SS1_{AVG}$, while the one-beat average shear stress $SS_{AVG}$ calculated by the second blood shear stress calculating means 132 is represented by $SS2_{AVG}$.

The index value calculating means 114 is configured to extract a maximum value $R_{MAX}$ (%) [$=100 \times (d_{MAX}-d_a)/d_a$] from the values of the diameter change ratio R of the blood vessel 20 measured by the blood vessel diameter measuring means 110, after expiration of the above-described blood vessel diameter measuring time period TIME1, that is, after termination of the measurement of the blood vessel lumen diameter $d_1$ by the blood vessel diameter measuring means 110 after releasing of the blood vessel 20 from the blood flow obstruction. The index value calculating means 114 then calculates a ratio between a value $SS_X$ (blood shear stress-related value $SS_X$) relating to the blood shear stress SS calculated by the first blood shear stress calculating means 124 or second blood shear stress calculating means 132, and the above-described maximum value $R_{MAX}$ (maximum blood vessel diameter change ratio value $R_{MAX}$) of the diameter change ratio of the blood vessel 20 calculated after the blood vessel releasing, and displays the calculated maximum blood vessel diameter change ratio value $R_{MAX}$ on the monitoring image display device 30. Either one of blood shear stress-related value $SS_X$ and the maximum blood vessel diameter change ratio value $R_{MAX}$ may be the denominator of the ratio to be calculated. For instance, the index value calculating means 114 calculates the ratio the denominator of which is the blood shear stress-related value $SS_X$. For example, the above-described blood shear stress-related value $SS_X$ is a maxim value of the blood shear stress SS calculated by the first blood shear stress calculating means 124 or the second blood shear stress calculating means 132, the one-beat average shear stress $SS_{AVG}$ obtained immediately after the blood vessel releasing from the blood flow obstruction or at a predetermined point of time after the blood vessel releasing, or an average of values of the blood shear stress SS obtained for a predetermined number of the heart beats.

Figure 12:
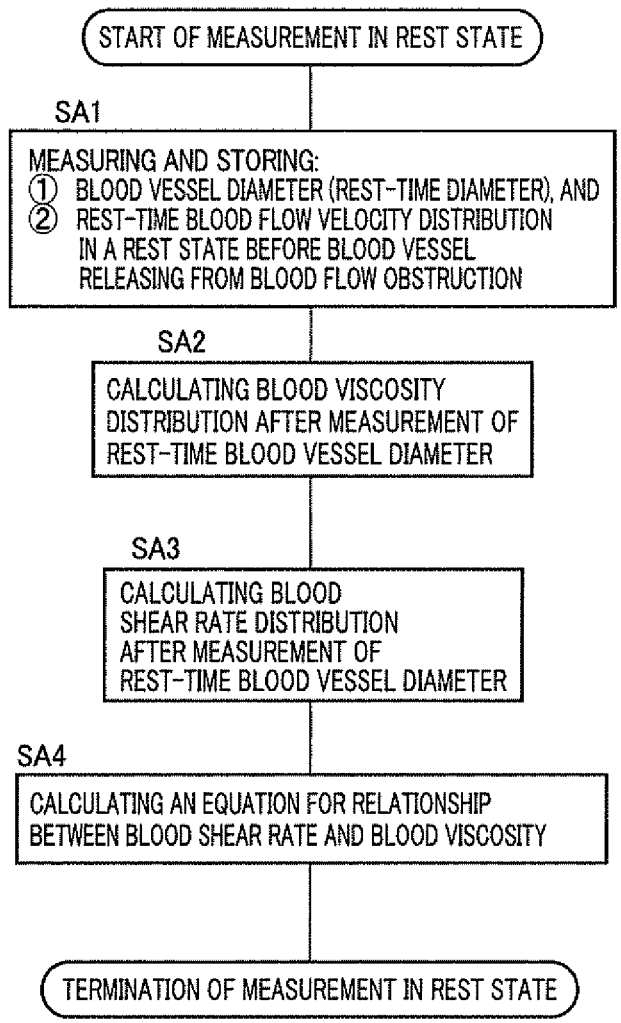
FIG. 12 is a flow chart illustrating a major control operation of the blood vessel function inspecting apparatus of FIG. 1, namely, a control operation performed according to the first embodiment to calculate the relationship between the blood viscosity and the blood shear rate on the basis of results of measurement at rest before releasing of the blood vessel from the blood flow obstruction.

FIG. 12 is the flow chart illustrating a major control operation of the blood vessel function inspecting apparatus 22 (electronic control device 28), namely, a control operation to calculate the viscosity-shear rate relationship VCSR on the basis of the results of measurements at rest before releasing of the blood vessel from the blood flow obstruction. This control operation according to the flow chart is performed at rest before releasing of the blood vessel from the blood flow obstruction.

Initially, step SA1 (hereinafter "step" being omitted) corresponding to the blood flow velocity measuring means 102 and the blood vessel diameter measuring means 110 is implemented to synthesize an image on the basis of the ultrasonic waves irradiated from the first short-axis ultrasonic detector array A of the ultrasonic probe 24 toward the blood vessel 20 within the vital body 14, in a rest state of the vital body 14 before releasing of the blood vessel 20 from the blood flow obstruction. The blood vessel rest-time diameter $d_a$ is measured from the synthesized image in a non-invasion manner and stored in memory. Further, the rest-time blood flow velocity distribution $DS_{RT}$ is measured on the basis of the ultrasonic waves irradiated from the long-axis ultrasonic detector array C of the ultrasonic probe 24 toward the blood vessel 20 within the vital body 14, in the rest state of the vital body 14 before releasing of the blood vessel 20 from the blood flow obstruction. It is noted that an echo transmitted and received in the direction of the $y_0$ axis indicated in FIG. 7 is used to measure the blood vessel lumen diameter $d_1$, and an echo transmitted and received in the direction of the y axis indicated in FIG. 7 is used to measure the blood flow velocity SPD.

In SA2 corresponding to the blood viscosity distribution calculating means 106, the rest-time blood viscosity distribution $DV_{RT}$ is calculated on the basis of the rest-time blood flow velocity distribution $DS_{RT}$ measured in SA1.

In SA3 corresponding to the blood shear rate distribution calculating means 108, the rest-time blood shear rate distribution $DSR_{RT}$ is calculated on the basis of the rest-time blood flow velocity distribution $DS_{RT}$ calculated in SA1.

In SA4 corresponding to the viscosity-shear rate relationship calculating means 104, the above-described viscosity-shear rate relationship VCSR is calculated on the basis of the values of the blood viscosity μ and the values of the blood shear rate SR, which are respectively extracted from the predetermined plurality of points within the above-described rest-time blood viscosity distribution $DV_{RT}$ and rest-time blood shear rate distribution $DSR_{RT}$. The above-described viscosity-shear rate relationship VCSR is calculated before releasing of the blood vessel from the blood flow obstruction. The viscosity-shear rate relationship VCSR is calculated as an equation such as the above-indicated Equation (8), which represents the relationship between the blood viscosity μ and the blood shear rate SR.

Figure 13:
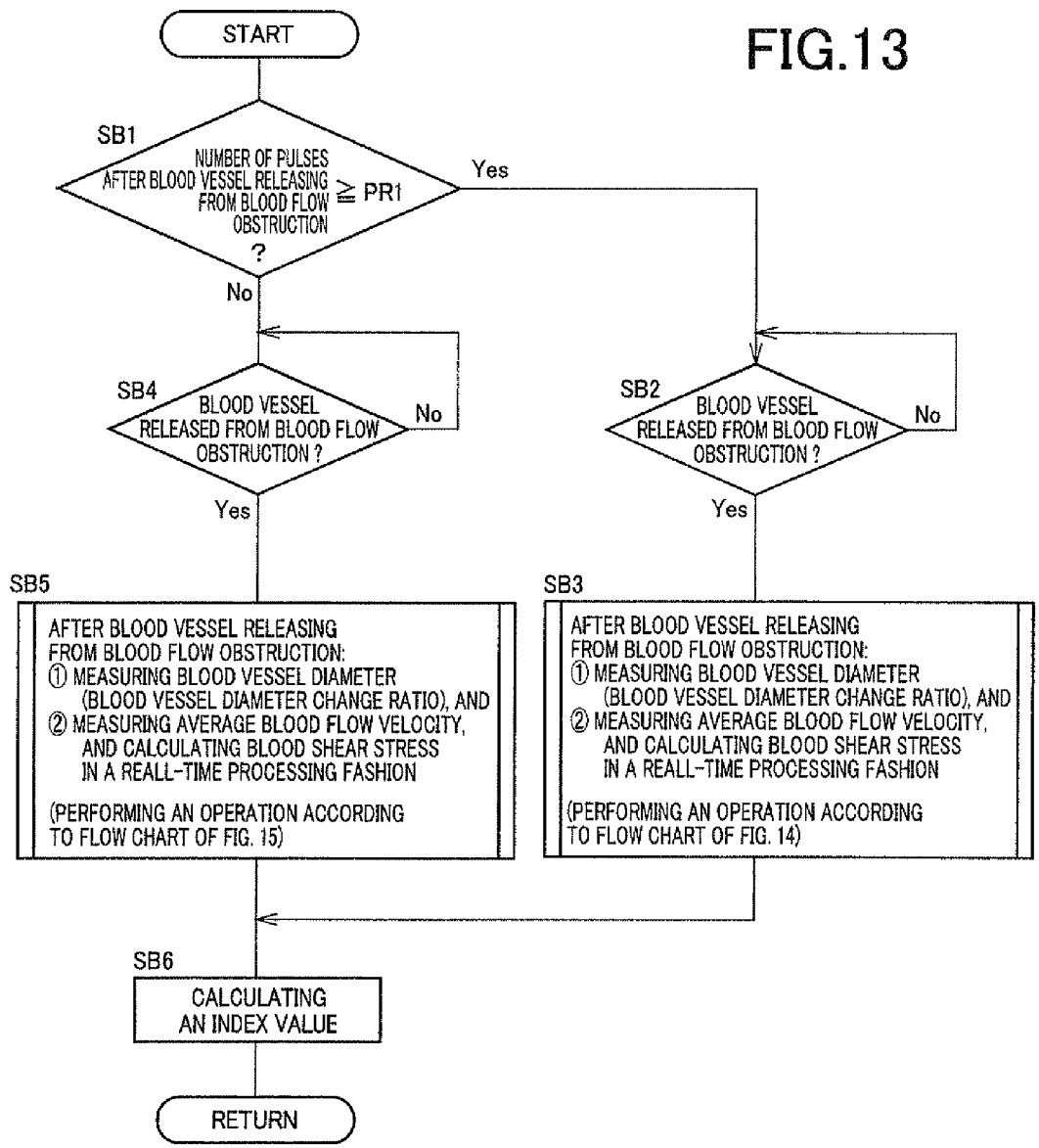
FIG. 13 is a flow chart illustrating a major control operation of the blood vessel inspecting apparatus of FIG. 1, namely, a control operation performed according to the first embodiment after calculation of the viscosity-shear rate relationship in SA4 of the flow chart of FIG. 12, to calculate a blood shear stress in a real-time processing fashion concurrently with the measurement of the blood flow velocity, after releasing of the blood vessel from the blood flow obstruction.

FIG. 13 is the flow chart illustrating a major control operation of the blood vessel inspecting apparatus 22 (electronic control device 28), namely, a control operation performed to calculate the blood shear stress SS in a real-time processing fashion concurrently with the measurement of the blood flow velocity SPD, after releasing of the blood vessel from the blood flow obstruction. The control operation according to this flow chart is performed after calculation of the viscosity-shear rate relationship VCSR in SA4 of FIG. 12. In this connection, it is noted that the control operation according to the flow chart of FIG. 13 is preferably initiated as soon as possible after the measurement of the rest-time blood flow velocity distribution $DS_{RT}$ in SA1 of FIG. 12, in order to maintain a high degree of accuracy of the viscosity-shear rate relationship VCSR calculated in the above-indicated SA4.

In SB1 corresponding to the blood flow velocity measurement implementation determining means 116, a determination as to whether the above-described release-time pulse number PR is equal to or larger than the above-described threshold value PR1. The above-described release-time pulse number PR used to make the determination in SB1 immediately before the blood vessel releasing from the blood flow obstruction is measured at a timing so as to permit the measurement of the blood flow velocity SPD in SB3 or SB5 immediately after the blood vessel releasing, more specifically, measured immediately before, that is, a predetermined short time before the moment of releasing of the blood vessel. If an affirmative determination is obtained in SB1, that is, if the above-described release-time pulse number PR is equal to or larger than the above-described threshold value PR1, the control flow goes to SB2. If a negative determination is obtained in SB1, the control flow goes to SB4.

SB2 is implemented to determine whether the blood vessel has been released from the blood flow obstruction, for the FMD evaluation. For instance, an affirmative determination in SB2 that the blood vessel has been released from the blood flow obstruction is made when the control signal is generated from the cuff pressure control portion 56 (cuff pressure control means 56) to lower the above-described cuff pressure to the atmospheric pressure for releasing the blood vessel. In the example of the time chart of FIG. 4, the negative determination is obtained in SB2 before the point of time t1, and the affirmative determination is obtained in SB2 at the point of time t1. If the positive determination is obtained in SB2, that is, if the releasing of the blood vessel is implemented, SB3 is executed.

SB3 is implemented to measure the diameter change ratio R of the blood vessel 20 after releasing of the blood vessel 20, and the average blood flow velocity $SPD_{AVG}$ within the blood vessel 20, and to calculate the blood shear stress SS in the real-time processing fashion on the basis of the average blood flow velocity $SPD_{AVG}$. Described more specifically, a control operation illustrated in the flow chart of FIG. 14 is performed in SB3.

Figure 14:
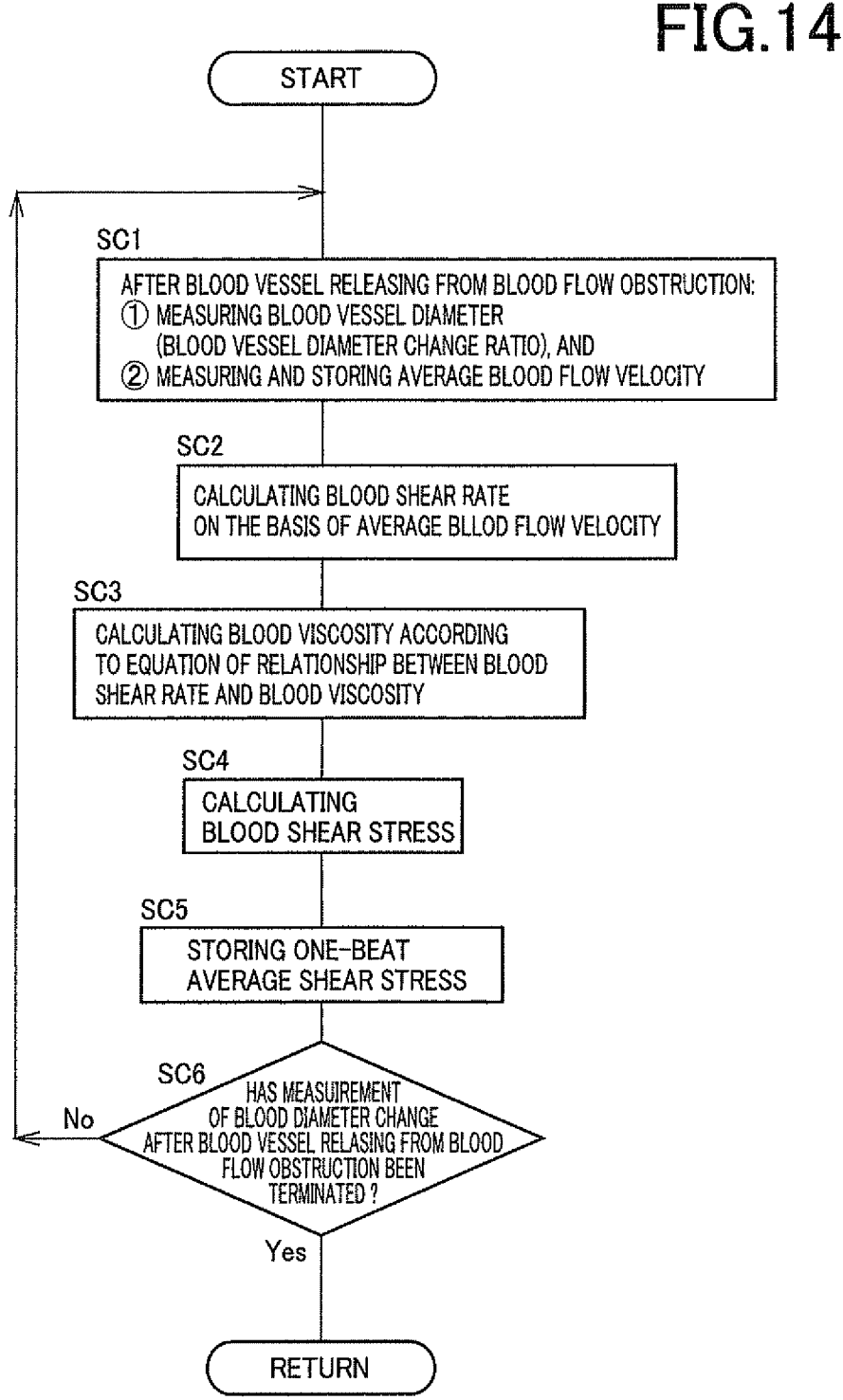
FIG. 14 is a flow chart illustrating a major control operation performed in SB3 of FIG. 13, namely, a control operation performed according to the first embodiment to measure a diameter change ratio of the blood vessel and an average blood flow velocity after releasing of the blood vessel from the blood flow obstruction, and calculate the blood shear stress in a real-time processing fashion on the basis of the average blood flow velocity.

FIG. 14 is the flow chart illustrating a major control operation performed in SB3 of FIG. 13, namely, a control operation performed to measure the diameter change ratio R of the blood vessel 20 and the average blood flow velocity $SPD_{AVG}$ after releasing of the blood vessel 20 from the blood flow obstruction, an calculate the blood shear stress SS in the real-time processing fashion on the basis of the average blood flow velocity $SPD_{AVG}$. The control operation according to the flow chart of FIG. 14 is repeatedly performed with an extremely short cycle time within a range from about several milliseconds to about several tens of milliseconds, for example.

In SC1 of FIG. 14, the blood vessel lumen diameter $d_1$ is measured, and the diameter change rate R of the blood vessel 20 is calculated and measured from the measured blood vessel lumen diameter $d_1$ and the above-described rest-time diameter $d_a$. Further, the average blood flow velocity $SPD_{AVG}$ within the blood vessel 20 is measured and stored in memory, concurrently with measurement of the above-described diameter change rate R of the blood vessel. In the present embodiment, the above-described average blood flow velocity $SPD_{AVG}$ is an average of the instantaneous values of the blood flow velocity SPD within the blood vessel 20 during a time period corresponding to one heart beat. It will be understood that the SC1 corresponds to the blood vessel diameter measuring means 110 and the first blood flow velocity measuring means 118.

In SC2 corresponding to the first blood shear rate calculating means 120, the blood shear rate SR is calculated on the basis of the average blood flow velocity $SPD_{AVG}$ measured in the above-described SC1 in a real-time processing fashion.

In SC3 corresponding to the first blood viscosity calculating means 122, the blood viscosity μ is calculated in a real-time processing fashion on the basis of the blood shear rate SR calculated in the above-described SC2, and according to the above-described viscosity-shear rate relationship VCSR (e.g. an equation of relationship between the blood viscosity μ and the blood shear rate SR) calculated in SA4 of FIG. 12 in advance of the blood vessel releasing from the blood flow obstruction.

In SC4 corresponding to the first blood shear stress calculating means 124, the blood shear stress SS is calculated in a real-time processing fashion on the basis of the blood shear rate SR calculated in the above-described SC2 and the blood viscosity μ calculated in the above-described SC3, and according to the Newton's law of viscosity represented by the above-indicated Equation (10).

In SC5 corresponding to the first blood shear stress calculating means 124, the blood shear stress SS calculated in SC4 is stored in a memory device, and the calculated blood shear stress SS is immediately displayed on the monitoring image display device 30. Since the blood shear stress SS calculated in SC4 is calculated on the basis of the average blood flow velocity $SPD_{AVG}$ measured as an average of the values of the blood flow velocity SPD during a time period of each heart beat, and can therefore be the above-described to be the above-described one-beat average shear stress $SS_{AVG}$.

In SC6, a determination as to whether the measurement of the blood vessel lumen diameter $d_1$ (measurement of the diameter change ratio R) for the FMD evaluation after the blood vessel releasing from the blood flow obstruction has been terminated. Described more specifically, a determination as to whether the above-described blood vessel diameter measuring time period TIME1 after the blood vessel releasing from the blood flow obstruction has expired is made, since the measurement of the blood vessel lumen diameter $d_1$ is terminated upon expiration of the blood vessel diameter measuring time period TIME1. If the determination in SC6 is positive, namely, the control operation according to the flow chart of FIG. 14 is terminated when the above-described blood vessel diameter measuring time period TIME1 has expired. If a negative determination is obtained in SC6, on the other hand, the control flow goes back to SC1. Accordingly, the above-described steps SC1 through SC5 are repeatedly implemented until the above-described blood vessel diameter measuring time period TIME1 after the blood vessel releasing has expired.

Referring back to FIG. 13, SB4 is implemented to determine whether the blood vessel has been released from the blood flow obstruction for the FMD evaluation, as in the above-described SB2. If an affirmative determination is obtained in this SB4, that is, if the blood vessel has been released from the blood flow obstruction, SB5 is implemented.

SB5 is implemented to make the measurement of the diameter change ratio R of the blood vessel 20 after the blood vessel releasing from the blood flow obstruction, the measurement of the blood flow velocity distribution DS2 within the blood vessel 20 after the blood vessel releasing, and the calculation of the blood shear stress SS in the real-time fashion on the basis of the blood flow velocity distribution DS2 after the blood vessel releasing. Described more specifically, a control operation according to the flow chart of FIG. 15 is performed in SB5.

Figure 15:
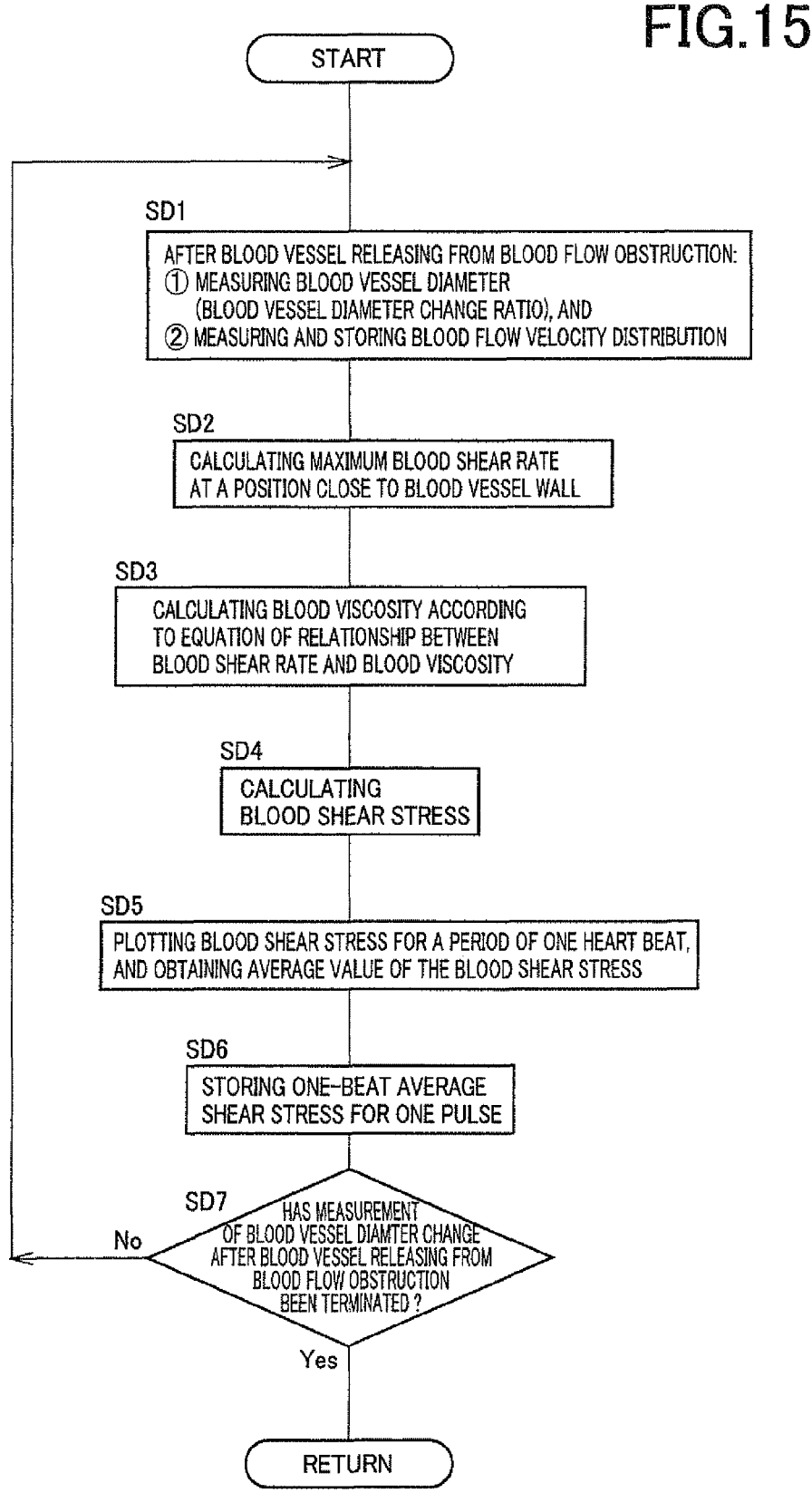
FIG. 15 is a flow chart illustrating a major control operation performed in SB5 of FIG. 13, namely, a control operation performed according to the first embodiment to calculate the diameter change ratio of the blood vessel and the post-release blood flow velocity distribution after releasing of the blood vessel from the blood flow obstruction, and to calculate the blood shear stress in a real-time processing fashion on the basis of the post-release blood flow velocity distribution.

FIG. 15 is the flow chart illustrating a major control operation performed in SB5 of FIG. 13, namely, the control operation performed to calculate the diameter change ratio R of the blood vessel 20 and the post-release blood flow velocity distribution DS2 after releasing of the blood vessel 20 from the blood flow obstruction, and to calculate the blood shear stress SS in a real-time processing fashion on the basis of the post-release blood flow velocity distribution DS2. The control operation according to the flow chart of FIG. 15 is repeatedly performed with an extremely short cycle time within a range from about several milliseconds to about several tens of milliseconds, for example.

In SD1 of FIG. 15, the blood vessel lumen diameter $d_1$ (diameter change ratio R) is measured. This measurement is similar to that in SC1 of FIG. 14. Further, the post-release blood flow velocity distribution DS2 within the blood vessel 20 after the blood flow releasing from the blood flow obstruction is measured and stored in memory, concurrently with the measurement of the above-described diameter change ratio R of the blood vessel 20. It will be understood that SD1 corresponds to the blood vessel diameter measuring means 110 and the second blood flow velocity measuring means 126.

In SD2 corresponding to the second blood shear rate calculating means 128, the maximum value $SR2_{MAX}$ of the blood shear rate SR is calculated in a real-time fashion on the basis of the post-release blood flow velocity distribution DS2 measured in the above-described SD1. Described more specifically, the maximum value $SR2_{MAX}$ of the blood shear rate SR is calculated from the blood shear rate distribution DSR calculated on the basis of the post-release blood flow velocity distribution DS2. For instance, the blood shear rate SR within the blood shear rate distribution DSR is considered to be highest at positions close to the wall of the blood vessel 20.

In SD3 corresponding to the second blood viscosity calculating means 130, the blood viscosity $\mu$ is calculated in a real-time processing fashion on the basis of the maximum value $SR2_{MAX}$ of the blood shear rate SR calculated in the above-described SD2, and according to the above-described viscosity-shear rate relationship VCSR (e.g, an equation of relationship between the blood viscosity $\mu$ and the blood shear rate SR) calculated in SA4 of FIG. 12 in advance of the blood vessel releasing from the blood flow obstruction.

In SD4, the blood shear stress SS is calculated in a real-time processing fashion on the basis of the maximum value $SR2_{MAX}$ of the blood shear rate SR calculated in the above-described SD2 and the blood viscosity $\mu$ calculated in the above-described SD3, and according to the Newton's law of viscosity represented by the above-indicated Equation (10).

In SD5, the values of the blood shear stress SS calculated in the above-described SD4 are chronologically averaged for each heart beat, to obtain the one-beat average shear stress $SS_{AVG}$. For example, the values of the blood shear stress SS calculated in the above-described SD4 are chronologically continuously plotted for a time period of one heart beat, and the integrated with the time, and the thus integrated value is divided by the above-indicated time period of one heart beat, to obtain the above-described one-beat average shear stress $SS_{AVG}$.

In SD6, the blood shear stress SS calculated in SD4 and the one-beat average shear stress $SS_{AVG}$ calculated in SD5 are stored in the memory device, and the calculated blood shear stress SS and the one-beat average shear stress $SS_{AVG}$ are immediately displayed on the monitoring image display device 30. It will be understood that SD4, SD5 and SD6 correspond to the second blood shear stress calculating means 132.

In SD7, a determination as to whether the above-described blood vessel diameter measuring time period TIME1 after the blood vessel releasing from the blood flow obstruction has expired is made as in SC6 of FIG. 14. If an affirmative determination is obtained in SD7, that is, if the above-described blood vessel diameter measuring time period TIME1 has expired, the control operation according to the flow chart of FIG. 15 is terminated. If a negative determination is obtained is obtained in SD7, on the other hand, the control flow goes back to SD1. Accordingly, the above-described steps SD1 through SD6 are repeatedly implemented until the above-described blood vessel diameter measuring time period TIME1 after the blood vessel releasing has expired.

Referring back to FIG. 13, SB6 corresponding to the index value calculating means 114 is implemented to calculate the index value relating to the dilatation function of the blood vessel 20 on the basis of the results of measurement or calculation in SB3 or SB5. Described more specifically, a maximum value $R_{MAX}$ of the diameter change ratio R of the blood vessel 20 is calculated from the diameter change ratio R calculated in SB3 or SB5. Further, the ratio between the above-described blood shear stress-related value $SS_X$ derived from the results of measurement in SB3 or SB5 and the above-described maximum value $R_{MAX}$ of the diameter change ratio R of the blood vessel 20 is calculated, and the calculated ratio is displayed on the monitoring image display device 30.

The present embodiment has the following advantages (A1) through (A10):

(A1) The present embodiment is configured such that (a) the blood vessel diameter measuring means 110 measures the change ratio R of the diameter (dilatation ratio R of the lumen diameter) of the blood vessel 20 in the live body 14 in the non-invasion manner with the ultrasonic waves irradiated toward the blood vessel 20 during the blood vessel diameter measuring time period TIME1 after releasing of the blood vessel from blood flow obstruction, (b) the blood flow velocity distribution measuring means 102 measures the blood flow velocity distribution DS (rest-time blood flow velocity distribution $DS_{RT}$) within the blood vessel in the non-invasion manner with the ultrasonic waves in advance before the blood vessel releasing from the blood flow obstruction, (c) the viscosity-shear rate calculating means 104 calculates the viscosity-shear rate relationship VCSR between the blood viscosity $\mu$ and the blood shear rate SR, before the blood vessel releasing, on the basis of the rest-time blood flow velocity distribution $DS_{RT}$ measured by the blood flow velocity distribution calculating means 102, in advance of the measurement of the change ratio R of the diameter of the blood vessel 20, and (d) the blood shear stress calculating means 112 measures the blood flow velocity within the blood vessel 20 concurrently with the measurement of the change ratio R of the diameter of the blood vessel 20, within the above-descried blood vessel diameter measuring time period TIME1 after the above-described blood vessel releasing, and calculates the blood shear stress SS on the basis of the measured blood flow velocity SPD and according to the above-described viscosity-shear rate relationship VCSR. Accordingly, it is possible to calculate the above-described viscosity-shear rate relationship VCSR specific to the blood vessel 20 and the blood under inspection, on the basis of the state of flow of the blood through the blood vessel 20. Therefore, it is possible to accurately calculate the blood shear stress SS according to this viscosity-shear rate relationship VCSR. Further, it is possible to evaluate the blood viscosity $\mu$ and the blood shear stress SS with a high degree of chronological and spatial consistency. In addition, once the above-described viscosity-shear rate relationship VCSR is calculated, the blood shear stress SS can be subsequently calculated with a low load of arithmetic operation. Furthermore, it is possible to compare and evaluate a plurality of results of the FMD inspection by reference to the blood shear stress SS, for example, which represents an amount of stimulus that causes dilatation of the blood vessel diameter after the blood vessel releasing from the blood flow obstruction. Further, it is possible to compensate the results of the FMD inspection, by the blood shear stress SS representing the amount of the stimulus, so that the calculation of the blood shear stress SS permits an improvement of the accuracy of repetition of the FMD inspection.

In addition, the blood flow velocity distribution calculating means 102 measures the rest-time blood flow velocity distribution $DS_{RT}$ before the blood vessel releasing from the blood flow obstruction, and the viscosity-shear rate relationship calculating means 104 calculates the above-described viscosity-shear rate relationship VCSR before the above-described blood vessel releasing, so that the viscosity-shear rate relationship VCSR has been obtained upon the blood vessel releasing (at the point of time t1 in FIG. 4). Accordingly, the blood shear stress SS can be calculated in the real-time processing fashion for the FMD evaluation, with a low load of arithmetic operation, concurrently with the measurement of the change ratio R of the diameter of the blood vessel 20 after the blood vessel releasing, without requiring calculations after the blood vessel releasing during a time period from the measurement of the blood flow velocity SPD to the measurement of the blood viscosity $\mu$, which calculations would cause a high load of arithmetic operation, such as a calculation according to the Navier-Stokes equations. Further, this manner of calculation of the blood shear stress SS in the real-time processing fashion makes it possible to obtain the blood shear stress SS immediately during the measurement, and to efficiently obtain the index value for the FMD inspection.

(A2) The present embodiment is further configured such that the blood shear stress calculating means 112 is provided with the first blood flow velocity calculating means 118, the first blood shear rate calculating means 120, the first blood viscosity calculating means 122, and the first blood shear stress calculating means 124. In this blood shear stress calculating means 112, (a) the first blood flow velocity measuring means 118 measures the average blood flow velocity $SPD_{AVG}$ within the blood vessel 20 during the predetermined blood vessel diameter measuring time period TIME1 after the releasing of the blood vessel from the blood flow obstruction, concurrently with the measurement of the change ratio R of the diameter of the blood vessel 20, (b) the first blood shear rate calculating means 122 calculates the blood shear rate SR on the basis of the average blood flow velocity $SPD_{AVG}$ measured by the first blood flow velocity measuring means 118, (c) the first blood viscosity calculating means 122 calculates the blood viscosity $\mu$ on the basis of the blood shear rate SR calculated by the first blood shear rate calculating means 120, and according to the viscosity-shear rate relationship VCSR calculated by the viscosity-shear rate relationship calculating means 104 in advance of the releasing of the blood vessel from the blood flow obstruction, and (d) the first blood shear stress calculating means 124 calculates the blood shear stress SS on the basis of the blood shear rate SR calculated by the first blood shear rate calculating means 120 and the blood viscosity $\mu$ calculated by the first blood viscosity calculating means 122. Accordingly, the measurement of the average blood flow velocity $SPD_{AVG}$ makes it possible to eliminate the calculation of the blood shear rate distribution DSR, for example, after the blood vessel releasing during a time period from the measurement of the average blood flow velocity $SPD_{AVG}$ to the calculation of the blood viscosity $\mu$, so that the load of arithmetic operation can be reduced. Accordingly, the blood shear stress SS can be calculated in the real-time processing fashion, concurrently with the measurement of the change ratio R of the diameter of the blood vessel 20 and the measurement of the average blood flow velocity $SPD_{AVG}$ after the blood vessel releasing, without requiring the apparatus to have a high capacity of arithmetic operation.

(A3) The present embodiment is further configured such that the first blood shear rate calculating means 120 calculates the blood shear rate SR by dividing the average blood flow velocity $SPD_{AVG}$ by the diameter of the blood vessel (e.g., blood vessel lumen diameter $d_1$). Accordingly, the blood shear rate SR can be efficiently calculated from the average blood flow velocity $SPD_{AVG}$, making it possible to reduce a load of arithmetic operation of the first blood shear rate calculating means 120. As a result, the electronic control device 28 can calculate the blood shear stress SS in the real-time processing fashion, concurrently with the measurement of the average blood flow velocity $SPD_{AVG}$, with a reduced load of arithmetic operation.

(A4) The present embodiment is further configured such that the average blood flow velocity $SPD_{AVG}$ is an average of the values of the blood flow velocity SPD for each heart beat, and the first blood shear stress calculating means 124 calculates the blood shear stress SS for each heart beat, so that the load of arithmetic operation can be made lower than in the case wherein a plurality of values of the blood shear stress SS are calculated during the time period of one heart beat.

(A5) The present embodiment is further configured such that the first blood shear stress calculating means 124 calculates the blood shear stress SS for each heart beat within the above-described blood vessel diameter measuring time period TIME1. Accordingly, the above-described blood shear stress SS can be calculated in the real-time processing fashion, so that the index value for the FMD inspection can be quickly obtained.

(A6) The present embodiment is further configured such that the blood viscosity distribution calculating means 106 and the blood shear rate distribution calculating means 108 of the viscosity-shear rate relationship calculating means 104 respectively calculate the blood viscosity distribution DV (rest-time blood viscosity distribution $DV_{RT}$) and the blood shear rate distribution DSR (rest-time blood shear rate distribution $DSR_{RT}$) on the basis of the blood flow velocity distribution $DS_{RT}$ measured by the blood flow velocity distribution measuring means 102, and the viscosity-shear rate relationship calculating means 104 calculates the above-described viscosity-shear rate relationship VCSR on the basis of values of the blood viscosity μ and values of the blood shear rate SR, which are extracted from the blood viscosity distribution $DV_{RT}$ and the blood shear rate distribution $DSR_{RT}$, respectively, and which respectively correspond to the plurality of predetermined points within the blood vessel 20. Accordingly, it is possible to more accurately calculate the above-described viscosity-shear rate relationship VCSR specific to the blood vessel 20 under inspection and the blood flowing through the blood vessel 20, so that the blood shear stress SS can be accurately calculated according to this viscosity-shear rate relationship VCSR.

(A7) The present embodiment is further configured such that the blood viscosity-shear rate distribution calculating means 106 calculates the rest-time blood viscosity distribution $DV_{RT}$ within the blood vessel 20 under measurement, on the basis of the above-described blood flow velocity distribution $DS_{RT}$ measured by the blood flow velocity distribution calculating means 102, and according to the Navier-Stokes equations which are stored in a memory and which are represented by the above-indicated Equations (2) and (3). Accordingly, the blood vessel function inspecting apparatus is practically operable to calculate the blood viscosity distribution $DV_{RT}$ on the basis of the blood flow velocity distribution $DS_{RT}$.

(A8) The present embodiment is further configured such that (a) the second blood flow velocity measuring means 126 measures the blood flow velocity distribution DS (post-release blood flow velocity distribution DS2) within the blood vessel 20 during the above-described blood vessel diameter measuring time period TIME1 after the above-described releasing of the blood vessel from the blood flow obstruction, concurrently with the measurement of the diameter change ratio R of the blood vessel 20 by the blood vessel diameter measuring means 110, (b) the second blood shear rate calculating means 128 calculates the maximum value $SR2_{MAX}$ of the blood shear rate SR on the basis of the post-release blood flow velocity distribution DS2 measured by the second blood flow velocity measuring means 126, (c) the second blood viscosity calculating means 130 calculates the blood viscosity μ on the basis of the maximum value $SR2_{MAX}$ of the blood shear rate SR calculated by the second blood shear rate calculating means 128, and according to the above-described viscosity-shear rate relationship VCSR calculated by the viscosity-shear rate relationship calculating means 104 in advance of the blood vessel releasing from the blood flow obstruction, and (d) the second blood shear stress calculating means 132 calculates the blood shear stress SS on the basis of the maximum value $SR2_{MAX}$ of the blood shear rate SR calculated by the second blood shear rate calculating means 128 and the blood viscosity μ calculated by the second blood viscosity calculating means 130, during the above-described blood vessel diameter measuring time period TIME1. The first blood flow velocity measuring means 118 measures the above-described average blood flow velocity $SPD_{AVG}$ if the blood flow velocity measurement implementation determining means 116 determines that the predetermined condition for changing the method of arithmetic operation is satisfied, and the second blood flow velocity measuring means 126 measures the above-described post-release blood flow velocity distribution DS2 if the blood flow velocity measurement implementation determining means 116 determines that the above-described condition for changing the method of arithmetic operation is not satisfied. Accordingly, the manner of calculating the blood shear stress SS can be changed according to the estimated load of arithmetic operation after the blood vessel releasing from the blood flow obstruction, for example, depending upon whether the predetermined condition for changing the method of arithmetic operation is satisfied or not, in view of a considered tendency that the load of arithmetic operation of the second blood shear stress calculating means 132 to calculate the blood shear stress SS is higher than that of the first blood shear stress calculating means 124, although the accuracy of calculation of the blood shear stress SS by the second blood shear stress calculating means 132 is higher than that by the first blood shear stress calculating means 124.

(A9) The present embodiment is further configured such that the index value calculating means 114 extracts the maximum value $R_{MAX}$ of the diameter change ratio R of the blood vessel 20 (maximum blood vessel diameter change ratio value $R_{MAX}$) from the values of the diameter change ratio R measured by the blood vessel diameter measuring means 110, after expiration of the above-described blood vessel diameter measuring time period TIME1, and calculates the ratio between the value $SS_X$ relating to the blood shear stress SS calculated by the first blood shear stress calculating means 124 or the second blood shear stress calculating means 132, and the calculated maximum blood vessel diameter change ratio value $R_{MAX}$. Accordingly, a result of measurement of the diameter change ratio R of the blood vessel 20 after the above-described releasing of the blood vessel 20 from the blood flow obstruction can be evaluated by reference to the blood shear stress SS. For instance, a plurality of results of the FMD inspection can be compared with each other and evaluated by reference to the blood shear stress SS.

(A10) The present embodiment is further configured such that the ultrasonic probe 24 which irradiates the ultrasonic waves toward the blood vessel 20 is provided with the long-axis ultrasonic detector array C having a plurality of ultrasonic oscillators arranged linearly in the longitudinal direction (direction of the $x_0$ axis) of the blood vessel 20, and the first short-axis ultrasonic detector array A and the second short-axis ultrasonic detector array B each of which has a plurality of ultrasonic oscillators arranged in the direction perpendicular to the longitudinal direction of the blood vessel 20, and the blood flow velocity SPD within the blood vessel 20 is measured with the ultrasonic waves irradiated from the long-axis ultrasonic detector array C, and the blood vessel diameter is measured with the ultrasonic waves irradiated from the first short-axis ultrasonic detector array A. Accordingly, it is possible to implement the measurement of the above-described blood flow velocity SPD (e.g., average blood flow velocity $SPD_{AVG}$ or blood flow velocity distribution DS) and the measurement of the diameter of the above-described blood vessel, concurrently with each other. In the present embodiment, the blood flow velocity SPD and the blood vessel lumen diameter $d_1$ (blood vessel diameter) may be measured by the long-axis ultrasonic detector array C, without using the first short-axis ultrasonic detector array A, such that the operation to measure the blood flow velocity SPD and the operation to measure the blood vessel lumen diameter $d_1$ are alternately performed with an extremely short cycle time. This modification has the same advantage as described above.

Another embodiment of this invention will be described next. In the following description, the same reference signs will be used to identify the same elements of the embodiments, the description of which is omitted.

Embodiment 2

In the first embodiment described above, the blood shear stress SS is calculated for the FMD evaluation, in the real-time processing fashion concurrently with the measurement of the average blood flow velocity $SPD_{AVG}$ or post-release blood flow velocity distribution DS2, during the above-described blood vessel diameter measuring time period TIME1 after the blood vessel releasing from the blood flow obstruction. In the present embodiment, the blood shear stress SS is not calculated in the real-time processing fashion, but is calculated in a batch processing fashion after completion of the measurement of the average blood flow velocity $SPD_{AVG}$. The following description of the present embodiment mainly relates to its aspects which are different from the first embodiment, and the description of the aspects which are identical with the first embodiment is omitted.

Figure 16:
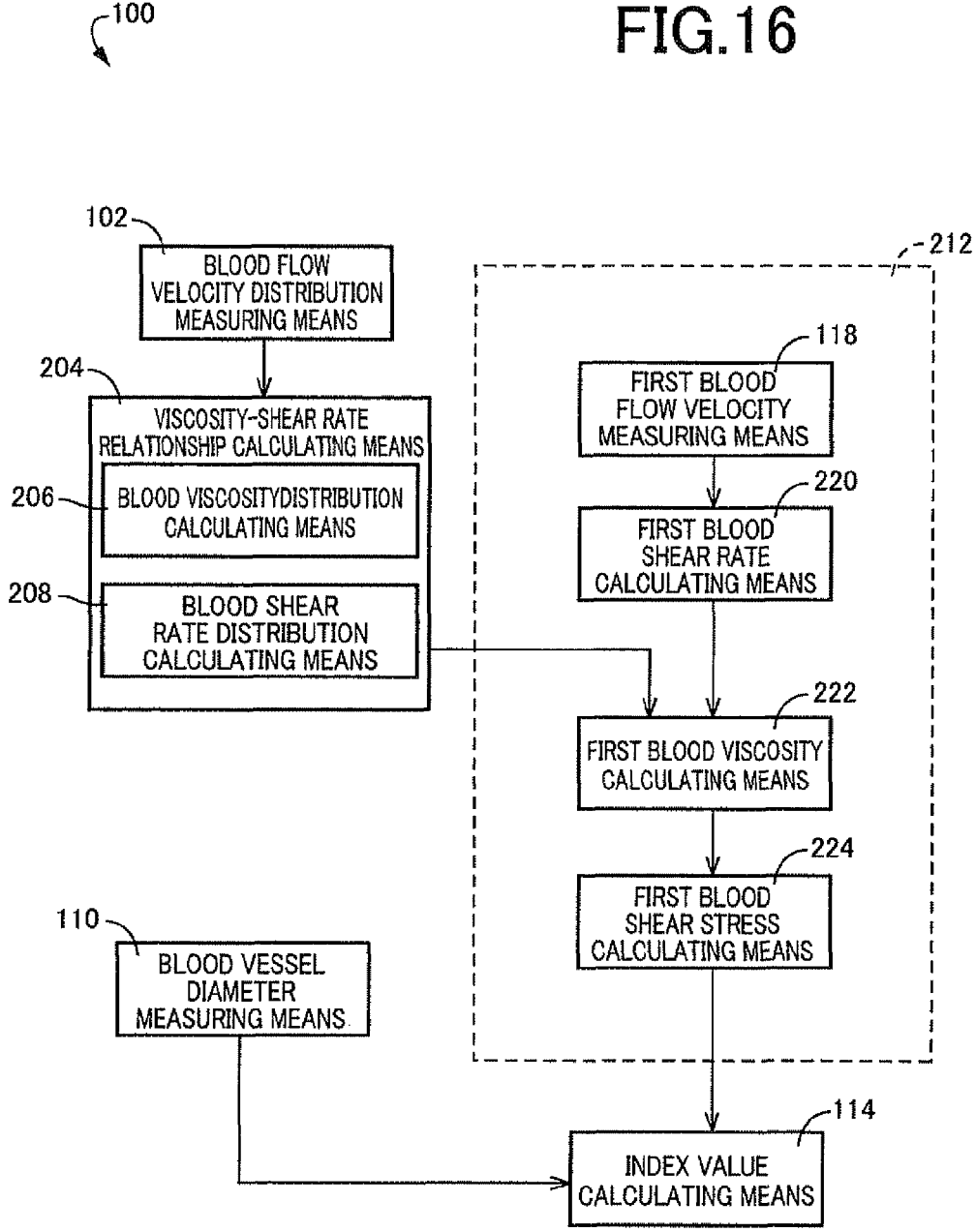
FIG. 16 is a functional block diagram corresponding to that of FIG. 5 according to the first embodiment, for explaining major control functions of the blood vessel function inspecting apparatus of FIG. 1 performed according to a second embodiment.

FIG. 16 is the functional block diagram corresponding to that of FIG. 5 according to the first embodiment, for explaining major control functions of the blood vessel function inspecting apparatus 22 (blood vessel function evaluating portion 100). Viscosity-shear rate relationship calculating means 204 shown in FIG. 16 is basically identical with the viscosity-shear rate relationship calculating means 104 in the first embodiment, but is different from the viscosity-shear rate relationship calculating means 104 in that the viscosity-shear rate relationship calculating means 204 calculates the above-described viscosity-shear rate relationship VCSR after expiration of the above-described blood vessel diameter measuring time period TIME1 after the blood vessel releasing from the blood flow obstruction, that is, after the measurement of the blood vessel lumen diameter $d_1$ by the blood vessel diameter measuring means 110 after the blood vessel releasing. In the present embodiment wherein the blood shear stress SS is calculated in the batch processing fashion, it is not necessary to calculate the viscosity-shear rate relationship VCSR in advance of the measurement of the diameter change ratio R of the blood vessel 20 after the blood vessel releasing.

Since the timings of calculation of the above-described viscosity-shear rate relationship VCSR are different in the present and first embodiments, blood viscosity distribution calculating means 206 provided in the viscosity-shear rate relationship calculating means 204 is basically identical with the blood viscosity distribution calculating means 106 in the first embodiment, but is different from the viscosity-shear rate distribution calculating means 106 in that the blood viscosity distribution calculating means 206 calculates the above-described rest-time blood viscosity distribution $DV_{RT}$ after expiration of the above-described blood vessel diameter measuring time period TIME1 after the blood vessel releasing from the blood flow obstruction.

Blood shear rate distribution calculating means 208 provided in the viscosity-shear rate relationship calculating means 204 is basically identical with the blood shear rate distribution calculating means 108 in the first embodiment, but is different from the blood shear rate distribution calculating means 108 in that the blood shear rate distribution calculating means 208 calculates the above-described rest-time blood shear rate distribution $DSR_{RT}$ after expiration of the above-described blood vessel diameter measuring time period TIME1 after the blood vessel releasing from the blood flow obstruction.

Blood shear stress calculating means 212 is basically identical with the blood shear stress calculating means 112 in the first embodiment, but is different from the blood shear stress calculating means 112 in that the blood shear stress calculating means 212 calculates the blood shear stress SS in the batch processing fashion after expiration of the above-described blood vessel diameter measuring time period TIME1 after the blood vessel releasing from the blood flow obstruction. Accordingly, the blood shear stress calculating means 212, which is provided with the first blood flow velocity measuring means 118, like the blood shear stress calculating means 112, is provided with first blood shear rate calculating means 220, first blood viscosity calculating means 222 and first blood shear stress calculating means 224 in place of the first blood shear rate calculating means 120, first blood viscosity calculating means 122 and first blood shear stress calculating means 124 of the first embodiment. The blood shear stress calculating means 212 is not provided with the blood velocity measurement implementation determining means 116, second blood velocity measuring means 126, second blood shear rate calculating means 128, second blood viscosity calculating means 130 and second blood shear stress calculating means 132 provided in the first embodiment, and is not provided with means corresponding to those means provided in the first embodiment. Accordingly, the present embodiment is not configured to make the determination as to whether the above-described condition for changing the method of arithmetic operation is satisfied or not, namely, the determination as to whether the above-described release-time pulse number PR is equal to or larger than the threshold value PR1, or not. Therefore, the first blood flow velocity measuring means 118 in the present embodiment measures the average blood flow velocity $SPD_{AVG}$ within the blood vessel 20 in the non-invasion manner, concurrently with the measurement of the diameter change ratio R of the blood vessel 20 by the blood vessel diameter measuring means 110, irrespective of the release-time pulse number PR.

The first blood shear rate calculating means 220 is basically identical with the first blood shear rate calculating means 120 in the first embodiment, but is different from the first blood shear rate calculating means 120 in that the first blood shear rate calculating means 220 calculates the blood shear rate SR in the batch processing fashion on the basis of the average blood flow velocity $SPD_{AVG}$ calculated by the first blood flow velocity measuring means 118, after expiration of the above-described blood vessel diameter measuring time period TIME1 after the blood vessel releasing from the blood flow obstruction, namely, after completion of the measurement of the average blood flow velocity $SPD_{AVG}$ after the blood vessel releasing.

The first blood viscosity calculating means 222 is basically identical with the first blood viscosity calculating means 122 in the first embodiment, but is different from the first blood viscosity calculating means 122 in that the first blood viscosity calculating means 222 calculates the blood viscosity μ in the batch processing fashion on the basis of the blood shear rate SR calculated by the first blood shear rate calculating means 220, after completion of the measurement of the average blood flow velocity $SPD_{AVG}$ after expiration of the above-described blood vessel diameter measuring time period TIME1 after the blood vessel releasing from the blood flow obstruction.

The first blood shear stress calculating means 224 is basically identical with the first blood shear stress calculating means 124 in the first embodiment, but is different from the first shear stress calculating means 124 in that the first blood shear stress calculating means 224 calculates the blood shear stress SS in the batch processing fashion on the basis of the blood shear rate SR calculated by the first blood shear rate calculating means 220 and the blood viscosity μ calculated by the first blood viscosity calculating means 222, after expiration of the above-described blood vessel diameter measuring time period TIME1 after the blood vessel releasing from the blood flow obstruction.

Figure 17:
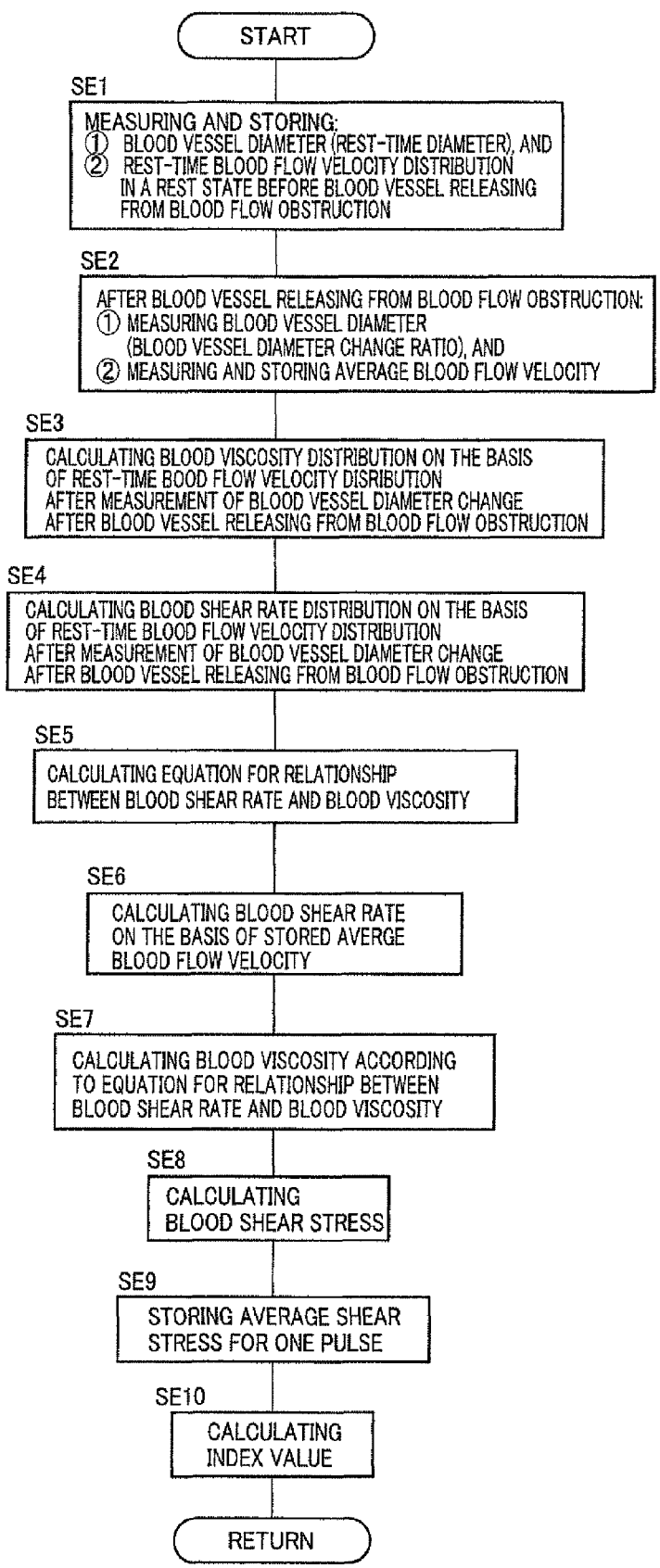
FIG. 17 is a flow chart corresponding to those of FIGS. 12 and 13 of the first embodiment, for explaining a major control operation of the blood vessel function inspecting apparatus of FIG. 1, namely, a control operation performed to calculate the blood shear stress in a batch processing fashion concurrently with the measurement of the diameter change ratio of the blood vessel after releasing of the blood vessel from the blood flow obstruction, for FMD evaluation of the blood vessel according to a second embodiment.

FIG. 17 is the flow chart corresponding to those of FIGS. 12 and 13 of the first embodiment, for explaining a major control operation of the blood vessel function inspecting apparatus 22 (electronic control device 28) according to the present embodiment, namely, a control operation performed to calculate the blood shear stress SS in the batch processing fashion concurrently with the measurement of the diameter change ratio R of the blood vessel 20 after releasing of the blood vessel 20 from the blood flow obstruction, for FMD evaluation of the blood vessel 20.

Like SA1 of FIG. 12, SE1 corresponding to the blood flow velocity distribution calculating means 102 and blood vessel diameter measuring means 110 is implemented to measure the rest-time diameter $d_a$ and the rest-time blood flow velocity distribution $DS_{RT}$, before the blood vessel releasing from the blood flow obstruction and when the subject is at rest.

Like SC1 of FIG. 14, SE2 corresponding to the blood vessel diameter measuring means 110 and the first blood flow velocity measuring means 118 is implemented to measure the blood vessel lumen diameter $d_1$ (diameter change ratio R of the blood vessel 20) and to measure the average blood flow velocity $SPD_{AVG}$, after the blood vessel releasing from the blood flow obstruction and until the above-described blood vessel diameter measuring time period TIME1 expires.

In SE3 corresponding to the blood viscosity distribution calculating means 206, the rest-time blood viscosity distribution $DV_{RT}$ is calculated on the basis of the rest-time blood flow velocity distribution $DS_{RT}$ measured in SE1. This rest-time blood viscosity distribution $DV_{RT}$ is calculated after expiration of the above-described blood vessel diameter measuring time period TIME1 after the blood vessel releasing from the blood flow obstruction.

In SE4 corresponding to the blood shear rate distribution calculating means 208, the rest-time blood shear rate distribution $DSR_{RT}$ is calculated on the basis of the rest-time blood flow velocity distribution $DS_{RT}$ measured in SE1. This rest-time blood shear rate distribution $DSR_{RT}$ is calculated after expiration of the above-described blood vessel diameter measuring time period TIME1 after the blood vessel releasing from the blood flow obstruction.

In SE5 corresponding to the viscosity-shear rate relationship calculating means 204, the above-described viscosity-shear rate relationship VCSR is calculated on the basis of the rest-time blood viscosity distribution $DV_{RT}$ calculated in SE3 and the rest-time blood shear rate distribution $DSR_{RT}$ calculated in SE4. SE5 is different from SE4 in FIG. 12 in that the above-described viscosity-shear rate relationship VCSR is calculated after expiration of the above-described blood vessel diameter measuring time period TIME1, but is identical with SA4 in FIG. 12 in the other aspects.

In SE6 corresponding to the first blood shear rate calculating means 220, the blood shear rate SR is calculated on the basis of the average blood flow velocity $SPD_{AVG}$ measured in SE2. SE6 is different from SC2 in FIG. 14 in that the above-described blood shear rate SR is calculated in the batch processing fashion after expiration of the above-described blood vessel diameter measuring time period TIME1, but is identical with SC2 in FIG. 14 in the other aspects.

In SE7 corresponding to the first blood viscosity calculating means 222, the blood viscosity μ is calculated on the basis of the blood shear rate SR calculated in SE6, and according to the above-described viscosity-shear rate relationship VCSR an equation of the relationship between the blood viscosity μ and the blood shear rate SR). SE7 is different from SC3 in FIG. 14 in that the above-described blood viscosity μ is calculated in the batch processing fashion after expiration of the above-described blood vessel diameter measuring time period TIME1, but is identical with SC3 in FIG. 14 in the other aspects.

In SE8 corresponding to the first blood shear stress calculating means 224, the blood shear stress SS is calculated on the basis of the blood shear rate SR calculated in SE6 and the blood viscosity calculated in SE7. SE8 is different from SC4 in FIG. 14 in that the above-described blood shear stress SS is calculated in the batch processing fashion after expiration of the above-described blood vessel diameter measuring time period TIME1, but is identical with SC4 in FIG. 14 in the other aspects.

In SE9 corresponding to the first blood shear stress calculating means 224, the blood shear stress SS (one-beat average shear stress $SS_{AVG}$) calculated in SE8 is stored in the memory device and displayed on the monitoring image display device 30.

SE10 corresponding to the index value calculating means 114 is similar to the S136 of FIG. 13.

The present embodiment wherein the blood shear stress SS is calculated in the batch processing fashion has the same advantages as the first embodiment, except the advantage of the first embodiment that the index value for the FMD evaluation can be efficiently obtained by calculating the blood shear stress SS in the real-time processing fashion.

While the embodiments of the present invention have been described in detail by reference to the drawings, for illustrative purpose only, it is to be understood that the invention may be embodied with various changes and improvements which may occur to those skilled in the art.

In the first embodiment described above, for example, the condition for changing the method of arithmetic operation is satisfied when the release-time pulse number PR is equal to or larger than the threshold value PR1. However, any suitable quantity other than the number of the heat beat pulses may be used to determine whether the condition for changing the method of arithmetic operation is satisfied or not.

In the illustrated embodiments, the above-described blood vessel diameter measuring time period TIME1 starts at the moment (point of time t1) of releasing of the blood vessel from the blood flow obstruction, as indicated in FIG. 4. However, this time period TIME1 may start at a point of time a suitable length of time after the moment of the blood vessel releasing, provided the time period TIME1 includes at least a point of time at which the blood vessel lumen diameter $d_1$ reaches the maximum value $d_{MAX}$. It is preferable that the blood shear stress calculating means 112 measures the blood flow velocity SPD immediately after the blood vessel releasing, even where the suitable length of time is provided between the moment of the blood vessel releasing and the start point of the blood vessel diameter measuring time period TIME1.

While the illustrated embodiments are configured such that the first blood flow velocity measuring means 118 calculates and measures the average blood flow velocity $SPD_{AVG}$ from the blood flow velocity distribution DS, the first blood flow velocity measuring means 118 may measure the average blood flow velocity $SPD_{AVG}$, without measuring the blood flow velocity distribution DS by ultrasonic Doppler effect measurement.

Although the illustrated embodiments are configured such that the average blood flow velocity $SPD_{AVG}$ measured by the first blood flow velocity measuring means 118 is an average of the values of the blood flow velocity SPD during the time period of each heart beat, any one of various time periods other than the time period of one heart beat may be used for the period of measurement of the average blood flow velocity $SPD_{AVG}$. For instance, the average blood flow velocity $SPD_{AVG}$ may be an average of the values of the blood flow velocity SPD during a time period corresponding to a predetermined number of heart beats, for instance, several heart beat pulses, or during a time period shorter than the time period of one heart beat. Alternatively, any quantity other than the number of heart beats may be used to define the time period for averaging the blood flow velocity SPD.

In the illustrated embodiment described above, the SB1, SB4 and SB5 of the flow chart may be eliminated. In this case, the control operation according to the flow chart of FIG. 13 is initiated with the SB2, and the control operation according to the flow chart of FIG. 15 is not performed.

It is noted that the brachium 16 shown in FIG. 1 in the illustrated embodiments is an upper arm of a human body.

In the illustrated embodiments, the blood vessel diameter measuring means 110 is configured to measure the blood vessel lumen diameter $d_1$ on the basis of an image synthesized with the ultrasonic waves irradiated from the first short-axis ultrasonic detector array A of the ultrasonic probe 24. However, the blood vessel lumen diameter $d_1$ may be measured on the basis of an image synthesized with the ultrasonic waves irradiated from the long-axis ultrasonic detector array C.

In the illustrated embodiments, the viscosity-shear rate relationship calculating means 104, 204 are configured to extract the values of the blood viscosity and the values of the blood shear rate SR from the above-described plurality of sampling points within the respective rest-time blood viscosity distribution $DV_{RT}$ and rest-time blood shear rate distribution $DSR_{RT}$, to calculate the above-described viscosity-shear rate relationship VCSR. The rest-time blood viscosity distribution $DV_{RT}$ and rest-time blood shear rate distribution $DSR_{RT}$ used for the extraction are preferably obtained in a specific phase of timing (at a specific point of time) within the time period of one heart beat. For example, the blood flow velocity SPD has a maximum or minimum value in the specific phase of timing within the time period of one heart beat.

Alternatively, the viscosity-shear rate relationship calculating means 104, 204 may be configured to calculate the above-described viscosity-shear rate relationship VCSR on the basis of the rest-time blood viscosity distribution $DV_{RT}$ and rest-time blood shear rate distribution $DSR_{RT}$ in a plurality of phases of timing within the time period of one heart beat, and to average a plurality of sets of the above-described viscosity shear rate relationship VCSR thus calculated, so that the averaged relationship VCSR is used by the first blood viscosity calculating means 122, 222 and the second blood viscosity calculating means 130 to calculate the blood viscosity μ.

Although the illustrated embodiments are configured such that the index value calculating means 114 is configured to calculate the ratio between the blood shear stress related value $SS_X$ and the maximum blood vessel diameter change ratio value $R_{MAX}$, after the blood vessel releasing from the blood flow obstruction, the maximum blood vessel diameter change ratio value $R_{MAX}$ may be replaced by any other parameter to calculate the index value (ratio). For instance, the maximum blood Vessel diameter change ratio value $R_{MAX}$ may be replaced by (i) a maximum value (unit: mm, for example) of an amount of change of the diameter of the blood vessel 20 after the blood vessel releasing, (ii) a delay time from the point of time t1 in FIG. 4 at which the blood vessel is released from the blood flow obstruction, to the point of time t2 at which the dilatation of the blood vessel 20 is initiated, or (iii) a transfer function where an input is selected from an amount or ratio of change of the diameter of the blood vessel 20 or a time constant of the diameter change, while an output is selected from the blood flow velocity SPD, a flow rate of the blood, the blood shear rate SR or the blood shear stress SS, or vice versa.

While the second embodiment described above is configured such that the blood flow velocity distribution measuring means 102 measures the rest-time blood flow velocity distribution $DS_{RT}$ before the blood vessel releasing from the blood flow obstruction, the blood flow velocity distribution measuring means 102 may measure the rest-time blood flow velocity distribution $DS_{RT}$ even after expiration of the above-described blood vessel diameter measuring time period TIME1 after the blood vessel releasing from the blood flow obstruction, provided this measurement of the rest-time blood flow velocity distribution $DS_{RT}$ is made before the measurement of the viscosity-shear rate relationship VCSR by the viscosity-shear rate relationship calculating means 204 after expiration of the above-described blood vessel diameter measuring time period TIME1, since the viscosity-shear rate relationship calculating means 204 in the second embodiment is configured to measure the viscosity-shear rate relationship VCSR after expiration of the above-described blood vessel diameter measuring time period TIME1

Although the second embodiment is configured such that the viscosity-shear rate relationship calculating means 204 calculates the above-described viscosity-shear rate relationship VCSR after expiration of the above-described blood vessel diameter measuring time period TIME1 after the blood vessel releasing from the blood flow obstruction, the viscosity-shear rate relationship calculating means 204 may calculate the viscosity-shear rate relationship VCSR before the above-described blood vessel releasing.

It is to be understood that the illustrated embodiments described above may be combined together, with specific features given priority of selection.

It is to be understood that the present invention may be embodied with various other changes not illustrated herein, without departing from the spirit of this invention.

NOMENCLATURE OF REFERENCE SIGNS

10: Sensor holder
20: Blood vessel
22: Blood vessel function inspecting apparatus
24: Ultrasonic probe
102: Blood flow velocity distribution measuring means
104: Viscosity-shear rate relationship calculating means 110: Blood vessel diameter measuring means
112: Blood shear stress measuring means
114: Index value calculating means
116: Blood flow velocity measurement implementation determining means
118: First blood flow velocity measuring means
120: First blood shear rate calculating means
122: First blood viscosity calculating means
124: First blood shear stress calculating means
126: Second blood flow velocity measuring means
128: Second blood shear rate calculating means
130: Second blood viscosity calculating means
132: Second blood shear stress calculating means
A: First short-axis ultrasonic detector array (Transverse ultrasonic detector array)
C: Long-axis ultrasonic detector array (Longitudinal ultrasonic detector array)

The invention claimed is:

1. A blood vessel function inspecting apparatus provided with a blood vessel diameter measuring portion configured to measure a change ratio of a diameter of a blood vessel within a live body in a non-invasion manner with ultrasonic waves irradiated toward the blood vessel during a predetermined blood vessel diameter measuring time period after releasing of the blood vessel from blood flow obstruction, the blood vessel function inspecting apparatus comprising:
a blood flow velocity distribution measuring portion configured to measure a blood flow velocity distribution within said blood vessel in a non-invasion manner with said ultrasonic waves before said releasing of the blood vessel from the blood flow obstruction or after said blood vessel diameter measuring time period;
a viscosity-shear rate relationship calculating portion configured to calculate a viscosity-shear rate relationship between a blood viscosity and a blood shear rate, on the basis of said blood flow velocity distribution measured by said blood flow velocity distribution measuring portion; and
a blood shear stress calculating portion configured to calculate a blood flow velocity within said blood vessel, concurrently with the measurement of said change ratio of the diameter of the blood vessel within said predetermined blood vessel diameter measuring time period after said releasing of the blood vessel from the blood flow obstruction, and calculating a blood shear stress on the basis of said calculated blood flow velocity, and according to said viscosity-shear rate relationship.

2. The blood vessel function inspecting apparatus according to claim 1, wherein said blood flow velocity distribution measuring portion measures said blood flow velocity distribution before said releasing of the blood vessel from the blood flow obstruction, and said viscosity-shear rate relationship calculating portion calculates said viscosity-shear rate relation before said releasing of the blood vessel from the blood flow obstruction.

3. The blood vessel function inspecting apparatus according to claim 2, wherein said blood shear stress calculating portion is provided with:
a first blood flow velocity measuring portion configured to measure an average blood flow velocity within said blood vessel during said predetermined blood vessel diameter measuring time period after said releasing of the blood vessel from the blood flow obstruction, concurrently with the measurement of the change ratio of the diameter of said blood vessel;
a first blood shear rate calculating portion configured to calculate the blood shear rate on the basis of said average blood flow velocity measured by said first blood flow velocity measuring portion;
a first blood viscosity calculating portion configured to calculate the blood viscosity on the basis of said blood shear rate calculated by said first blood shear rate calculating portion, and according to said viscosity-shear rate relationship calculated by said viscosity-shear rate relationship calculating portion; and
a first blood shear stress calculating portion configured to calculate the blood shear stress on the basis of said blood shear rate calculated by said first blood shear rate calculating portion and said blood viscosity calculated by said first blood viscosity calculating portion.

4. The blood vessel function inspecting apparatus according to claim 3, wherein said first blood shear rate calculating portion calculates said blood shear rate by dividing said average blood flow velocity by said diameter of the blood vessel.

5. The blood vessel function inspecting apparatus according to claim 4, wherein said average blood flow velocity is an average of values of the blood flow velocity within said blood vessel for each heart beat.

6. The blood vessel function inspecting apparatus according to claim 5, wherein said first blood shear stress calculating portion calculates said blood shear stress for each heart beat within said predetermined blood vessel diameter measuring time period.

7. The blood vessel function inspecting apparatus according to claim 3, wherein said blood shear stress calculating portion is provided with:
a second blood flow velocity measuring portion configured to measure the blood flow velocity distribution within said blood vessel during said predetermined blood vessel diameter measuring time period after said releasing of the blood vessel from the blood flow obstruction, concurrently with the measurement of the change ratio of the diameter of the blood vessel;
a second blood shear rate calculating portion configured to calculate a maximum value of the blood shear rate on the basis of said blood flow velocity distribution measured by said second blood flow velocity measuring portion;
a second blood viscosity calculating portion configured to calculate the blood viscosity on the basis of said maximum value of the blood shear rate calculated by said second blood shear rate calculating portion, and according to said viscosity-shear rate relationship calculated by said viscosity-shear rate relationship calculating portion; and
a second blood shear stress calculating portion configured to calculate the blood shear stress on the basis of said maximum value of the blood shear rate calculated by said second blood shear rate calculating portion and said blood viscosity calculated by said second blood viscosity calculating portion, during said predetermined blood vessel diameter measuring time period,
and wherein said first blood flow velocity measuring portion measures said average blood flow velocity if a predetermined condition for changing a method of arithmetic operation is satisfied, and said second blood flow velocity measuring portion measures said blood flow velocity distribution if said predetermined condition for changing the method of arithmetic operation is not satisfied.

8. The blood vessel function inspecting apparatus according to claim 7, further comprising an index value calculating portion configured to calculate a ratio between a value relating to said blood shear stress calculated by said first blood shear stress calculating portion or said second blood shear stress calculating portion, and a maximum value of the change ratio of the diameter of said blood vessel after said releasing of the blood vessel from the blood flow obstruction measured by said blood vessel diameter measuring portion.

9. The blood vessel function inspecting apparatus according to claim 1, wherein said viscosity-shear rate relationship calculating portion calculates a distribution of the blood viscosity and a distribution of the blood shear rate on the basis of said blood flow velocity distribution measured by said blood flow velocity measuring portion, and calculates said viscosity-shear rate relationship on the basis of values of the blood viscosity and values of the blood shear rate, which are extracted from said distribution of the blood viscosity and said distribution of the blood shear rate, respectively, and which respectively correspond to a plurality of predetermined points within said blood vessel.

10. The blood vessel function inspecting apparatus according to claim 9, wherein said viscosity-shear rate relationship calculating portion calculates said blood viscosity distribution on the basis of said blood flow velocity distribution measured by said blood flow velocity distribution calculating portion, and according to Navier-Stokes equations stored in a memory.

11. The blood vessel function inspecting apparatus according claim 1, further comprising an ultrasonic probe which irradiates said ultrasonic waves toward said blood vessel and which is provided with a longitudinal ultrasonic detector array having a plurality of ultrasonic oscillators arranged linearly in a longitudinal direction of said blood vessel, and a transverse ultrasonic detector array having a plurality of ultrasonic oscillators arranged linearly in a direction perpendicular to the longitudinal direction of said blood vessel, and wherein said blood :flow velocity distribution measuring portion measures the blood flow velocity within said blood vessel with the ultrasonic waves irradiated from said longitudinal ultrasonic detector array, and said blood vessel diameter measuring portion measures the diameter of said blood vessel with the ultrasonic waves irradiated from said transverse ultrasonic detector array.

12. The blood vessel function inspecting apparatus according to claim 1 wherein an ultrasonic probe which irradiates said ultrasonic waves toward said blood vessel is provided with a longitudinal ultrasonic detector array having a plurality of ultrasonic oscillators arranged linearly in a longitudinal direction of said blood vessel, and wherein an operation of said longitudinal ultrasonic detector array to measure the blood flow velocity within said blood vessel and an operation of the longitudinal ultrasonic detector array to measure the diameter of said blood vessel are performed alternately with time.

* * * * *